(12) United States Patent
Kang et al.

(10) Patent No.: US 9,820,715 B2
(45) Date of Patent: Nov. 21, 2017

(54) X-RAY IMAGING APPARATUS AND METHOD FOR CONTROLLING THE SAME

(71) Applicant: SAMSUNG ELECTRONICS CO., LTD., Suwon-si (KR)

(72) Inventors: Dong-Goo Kang, Hwaseong-si (KR); Young Hun Sung, Hwaseong-si (KR); Sung W Jeon, Suwon-si (KR); Jaemock Yi, Hwaseong-si (KR); Jiyoung Choi, Suwon-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/838,652

(22) Filed: Aug. 28, 2015

(65) Prior Publication Data

US 2016/0206274 A1    Jul. 21, 2016

(30) Foreign Application Priority Data

Jan. 21, 2015    (KR) ........................ 10-2015-0009877

(51) Int. Cl.
*A61B 6/00* (2006.01)
*A61B 6/06* (2006.01)
*A61B 6/10* (2006.01)

(52) U.S. Cl.
CPC ............... *A61B 6/542* (2013.01); *A61B 6/06* (2013.01); *A61B 6/107* (2013.01); *A61B 6/4035* (2013.01); *A61B 6/4441* (2013.01); *A61B 6/487* (2013.01); *A61B 6/504* (2013.01); *A61B 6/547* (2013.01); *A61B 6/461* (2013.01)

(58) Field of Classification Search
CPC .................................. A61B 6/06; A61B 6/469
See application file for complete search history.

(56) References Cited

U.S. PATENT DOCUMENTS

| | | | |
|---|---|---|---|
| 4,103,176 A * | 7/1978 | Coyle | A61B 6/0414 378/204 |
| 2001/0019599 A1 * | 9/2001 | Guendel | A61B 6/032 378/15 |
| 2004/0264647 A1 | 12/2004 | Graf et al. | |
| 2008/0269588 A1 * | 10/2008 | Csavoy | A61B 34/20 600/407 |
| 2010/0272238 A1 | 10/2010 | Machan et al. | |
| 2011/0261926 A1 * | 10/2011 | Hangartner | A61B 6/032 378/19 |

* cited by examiner

*Primary Examiner* — Dani Fox
(74) *Attorney, Agent, or Firm* — Sughrue Mion, PLLC

(57) ABSTRACT

An X-ray imaging apparatus is provided. The X-ray imaging apparatus includes an X-ray source configured for irradiating X-rays to a subject; a filtering unit configured for controlling a dose of X-rays irradiated to the subject; and a processor configured for distinguishing and setting up an uninterested region in an X-ray image obtained based in the irradiated X-rays, and for controlling the filtering unit to set a dose of X-rays irradiated into the uninterested region.

22 Claims, 24 Drawing Sheets

X-RAY IMAGING APPARATUS AND METHOD FOR CONTROLLING THE SAME

CROSS-REFERENCE TO RELATED APPLICATION(S)

This application claims priority under 35 U.S.C. §119(a) from Korean Patent Application No. 10-2015-0009877, filed on Jan. 21, 2015 in the Korean Intellectual Property Office, the disclosure of which is incorporated herein by reference in its entirety.

BACKGROUND

1. Field

Exemplary embodiments relate to an X-ray imaging apparatus and a method for controlling the same, which irradiates X-rays toward a subject for imaging the inside of the subject.

2. Description of the Related Art

X-ray imaging apparatuses are devices which are configured for obtaining an image of the inside of a subject by irradiating X-rays toward the subject and using X-rays that propagate through the subject. Since the transmittance of X-rays varies based on characteristics of a material that makes up the subject, an internal structure of the subject may be imaged by detecting an intensity or strength of the X-rays that penetrate the subject.

In particular, X-ray video technologies which facilitate observation of movements that occur inside the subject have been actively applied in an intervention treatment, such as angiography, or an X-ray imaging field, such as X-ray fluoroscopy.

SUMMARY

Exemplary embodiments provide an X-ray imaging apparatus and a method for controlling the same, which sets up an uninterested region so as to reduce a dosage amount of X-rays to be irradiated to a user of the X-ray imaging apparatus.

In accordance with an aspect of one or more exemplary embodiments, an X-ray imaging apparatus is provided. The X-ray imaging apparatus includes an X-ray source configured to irradiate X-rays toward a subject; a filter configured to control a dosage amount of X-rays being irradiated toward the subject; and a processor configured to distinguish and set up an uninterested region in an X-ray image obtained based on the irradiated X-rays, and to control the filter to set the dosage amount of X-rays to be irradiated into the uninterested region.

In accordance with another aspect of one or more exemplary embodiments, a method for controlling an X-ray imaging apparatus is provided. The method includes obtaining an X-ray image by irradiating X-rays toward a subject; distinguishing and setting up an uninterested region in the X-ray image; and controlling a dosage amount of X-rays to be irradiated into the uninterested region by driving at least one filter.

Other aspects, advantages, and salient features will become apparent to those skilled in the art from the following detailed description, which, taken in conjunction with the annexed drawings, discloses exemplary embodiments.

BRIEF DESCRIPTION OF THE DRAWINGS

The above and other features and advantages will become more apparent by describing in detail exemplary embodiments thereof with reference to the attached drawings, in which.

Throughout the drawings, like reference numerals will be understood to refer to like parts, components, and structures.

DETAILED DESCRIPTION

Exemplary embodiments of an X-ray imaging apparatus and method for controlling the same will now be described in detail with reference to accompanying drawings.

Figure 1:
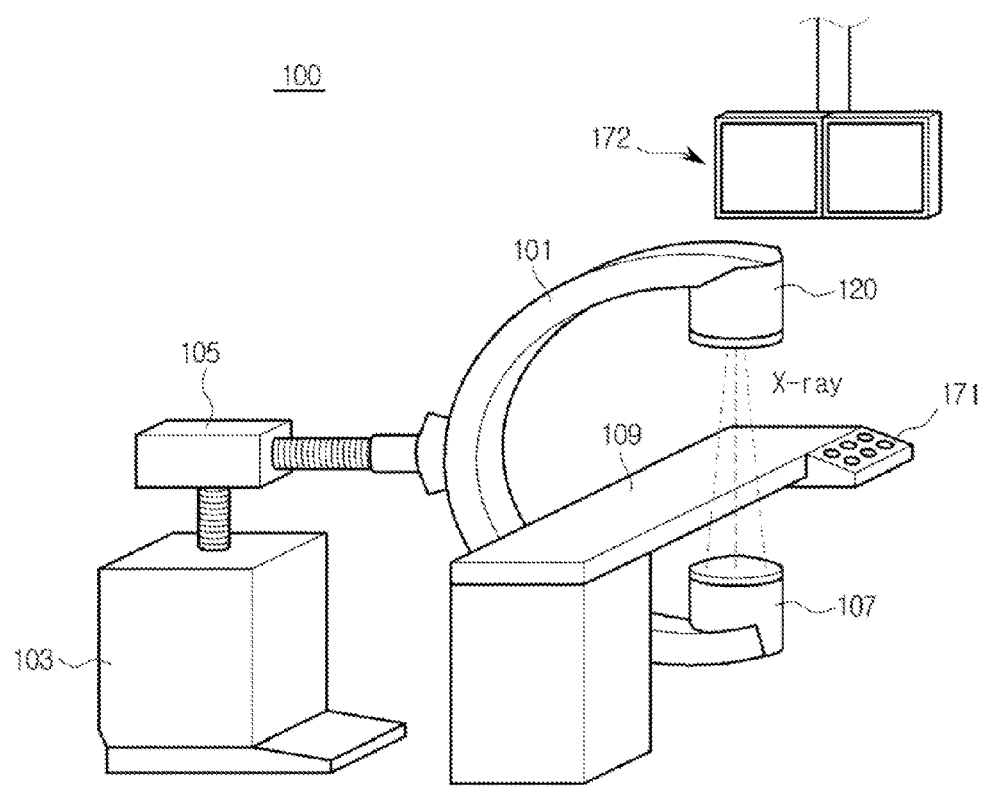
FIG. 1 is an exterior view of an X-ray imaging apparatus, according to an exemplary embodiment.
Figure 2:
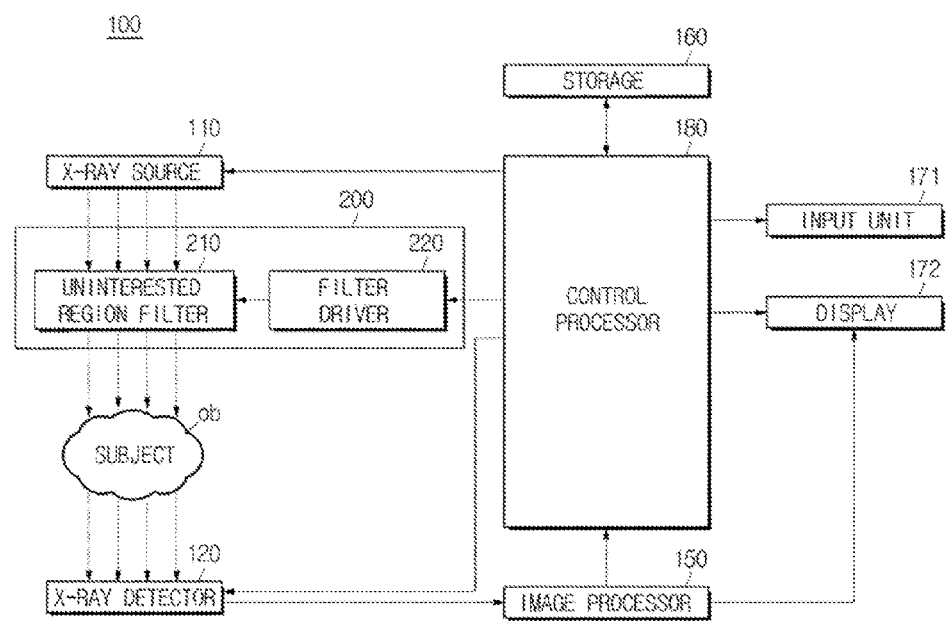
FIG. 2 is a control block diagram of an X-ray imaging apparatus, according to an exemplary embodiment.

FIG. 1 is an exterior view of an X-ray imaging apparatus, according to an exemplary embodiment, and FIG. 2 is a control block diagram of the X-ray imaging apparatus, according to an exemplary embodiment.

Referring to FIGS. 1 and 2, an X-ray imaging apparatus 100 may include an X-ray source 110 that is configured for irradiating X-rays to a subject ob, a filtering unit (also referred to herein as a "filter") 200 that is configured for controlling a dose (i.e., a dosage amount) of X-rays to be irradiated from the X-ray source 110, an X-ray detector 120 that is configured for detecting X-rays in order to obtain frame data, an image processor 150 that is configured for creating an X-ray image and/or an X-ray video based on the frame data, and a control processor 180 that is configured for controlling the components of the X-ray imaging apparatus 100.

The subject (or object) ob may refer to a target for X-ray scanning, the inside of which is to be X-ray imaged. For example, the subject ob may include internal organs, such as the liver, heart, uterus, brain, breast, stomach, etc., and/or blood vessels.

In an exemplary embodiment, the X-ray imaging apparatus 100 may have a C-arm structure. In particular, an X-ray generating assembly 107 having the X-ray source 110 and the X-ray detector 120 may be mounted at either end of a C-arm 101. The C-arm 101 may be connected to a main body 103 via a connecting shaft 105, and may be rotatable in the orbital direction.

There may be a table 109 arranged between the X-ray generating assembly 107 and the X-ray detector 120. The X-ray imaging apparatus 100 may obtain an X-ray image and/or an X-ray video by irradiating X-rays toward the subject ob lying on the table 109. For example, the X-ray imaging apparatus 100 may employ X-ray fluoroscopy in order to create an X-ray video, and may be applied to an X-ray diagnostics field, such as, for example, angiography, or any of various treatment fields that use an X-ray imaging apparatus.

The X-ray source 110 may be included in the X-ray generating assembly 107 and configured for irradiating X-rays toward the subject ob. The X-ray source 110 may be supplied with power from a power supply (not shown) in order to facilitate the generating of X-rays.

For obtaining an X-ray video, the X-ray source 110 may constantly irradiate X-rays toward the subject ob. A scheme for continuously irradiating X-rays by the X-ray source 110 may include a constant radiation scheme or a pulse radiation scheme.

The X-ray source 110 may constantly irradiate a lower dose of X-rays in the constant irradiation scheme, and continuously irradiate short pulses of X-ray in the pulse radiation scheme. Therefore, the pulse radiation scheme may help to reduce the dosage amount of X-rays and motion blurring. The X-ray imaging apparatus 100 may employ both of the two schemes, but for convenience of explanation, it is assumed that the following exemplary embodiments employ the pulse radiation scheme.

The X-ray source 110 may irradiate X-rays multiple times, at predetermined or arbitrary time intervals. The predetermined or arbitrary time interval may be determined based on pulse rates or frame rates. The pulse rate may be determined based on the frame rate or vice versa. The frame rate may be set, for example, to any of 30 frames per second (fps), 15 fps, 7.5 fps, etc. For example, if the frame rate is set to 15 fps, the pulse rate is set to 15 pulses per second (pps) and accordingly, X-rays may be produced 15 times in a second.

The X-ray source 110 may produce X-rays according to a scanning parameter set by the control processor 180. The scanning parameter may also referred to as an exposure parameter, and automatic control of the scanning parameter by the X-ray imaging apparatus 100 may be referred to as any of auto exposure control, automatic brightness control, automatic dose control, or automatic dose rate control.

The scanning parameter may include at least one selected from among a group which includes tube voltage, tube current, exposure time, filter type, frame rate, pulse rate, type of target material, and the like.

The scanning parameter may be determined based on an X-ray image obtained by the image processor 150, or based on advance information that is received before X-ray scanning. Exemplary embodiments of the former case will now be described in detail.

The control processor 180 may determine the scanning parameter by analyzing the X-ray image obtained by the image processor 150. For example, the control processor 180 may analyze the X-ray image to determine characteristics of the subject ob, such as thickness or density, and based on the determination result, determine the scanning parameter, such as tube voltage, tube current, exposure time, filter type, type of target material, etc., that matches the characteristics of the subject ob.

Furthermore, the control processor 180 may obtain as much information as possible about a movement of the subject ob or an object of interest by increasing the frame rate if the subject ob makes a relatively large movement or a movement of the object of interest that needs constant attention is relatively large, and may reduce exposure of the subject ob to radiation by decreasing the frame rate if a movement of the subject ob or the object of interest is relatively small.

The X-ray detector 120 may detect X-rays irradiated from the X-ray source 110, and obtain frame data by converting the detected X-rays to electric signals. The frame data refers to respective X-ray data obtained based on a frame rate of the X-ray imaging apparatus 110.

The X-ray detector 120 may have a two dimensional (2D) array structure with multiple pixels, and may obtain a piece of frame data by converting a respective X-ray which is detected for each pixel to an electric signal.

The X-ray detector 120 may employ any of various structures that detect and convert X-rays to electric signals. For example, the structure may include any of a direct scheme for directly converting X-rays to electric signals using photoconductors, such as amorphous selenium (a-Se), and an indirect scheme for converting X-rays to visible rays and then to electric signals by using a scintillator, such as cesium iodide (CsI).

The image processor 150 may create an X-ray image based on the frame data output from the X-ray detector 120.

The image processor 150 may perform pre-processing on the frame data before creating an X-ray image. For example, the image processor 150 may eliminate noise from the frame data, or compensate for inter-pixel errors of the X-ray detector 120.

The image processor 150 may create an X-ray video. As described above, when the X-ray source 110 irradiates X-rays in a predetermined cycle, the X-ray detector 120 may detect X-rays in synchronization with X-ray irradiation and continuously output frame data. The image processor 150 may use the frame data that is continuously output from the X-ray detector 120 to create multiple X-ray images, and then use the multiple X-ray images to create an X-ray video.

A storage 160 may store data required for operation of the X-ray imaging apparatus 100. For example, the storage 160 may store an operating system required to operate the X-ray imaging apparatus 100, and one or more applications.

Furthermore, the storage 160 may store data produced during an operation of the X-ray imaging apparatus 100. For example, the storage 160 may store frame data output from the X-ray detector 120, and/or X-ray images or X-ray videos output from the image processor 150.

The storage 160 may include any of a high-speed random access memory (RAM), a magnetic disk, a static RAM, a dynamic RAM, a read only memory (ROM), etc., but is not limited thereto.

Furthermore, the storage 160 may be detachable from the X-ray imaging apparatus 100. For example, the storage 160 may include any of a compact flash (CF) card, a secure digital (SD) card, a smart media (SM) card, a multimedia card (MMC), or a memory stick, but is not limited thereto.

A display 172 may display an X-ray image or X-ray video required for treatment or diagnosis of the user. The display 172 may also display information relating to the subject in order to facilitate the user's treatment, surgery, or diagnosis. The display 172 may be arranged separately from the X-ray imaging apparatus 100, as shown in FIG. 1, but is not limited thereto.

The display 172 may include a displaying means and/or a display device, such as any of a plasma display panel (PDP), a liquid crystal display (LCD) panel, a light emitting diode (LED) panel, an organic LED (OLED) panel, an active-matrix OLED (AMOLED) panel, etc., or a sound output means, such as a speaker, but is not limited thereto.

The X-ray imaging apparatus 100 may further include an input unit (also referred to herein as an "input device") 171. For example, the user may input information required, and/or control an operation of the X-ray imaging apparatus 100, via the input unit 171 mounted on the table 109.

The user may be a medical expert, e.g., a doctor, a nurse, a medical technologist, a medical image expert, etc., but is not limited thereto.

Figure 3:
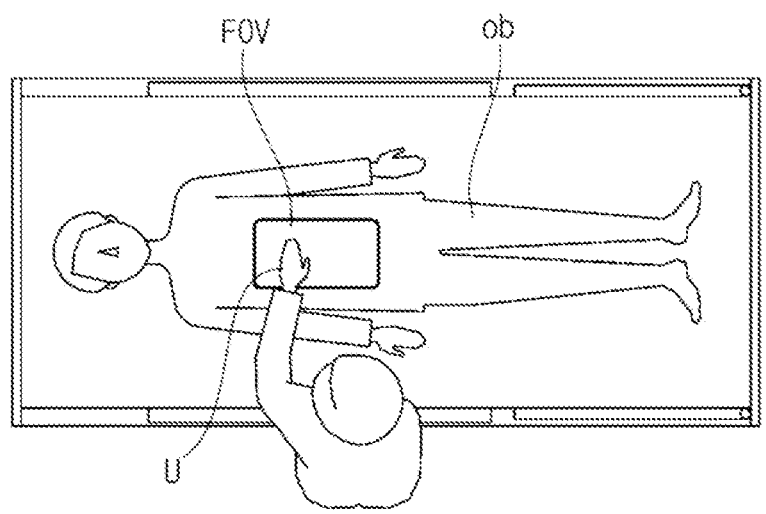
FIG. 3 illustrates a view for describing a region established on a subject.

FIG. 3 illustrates a view for describing a region established on a subject.

Referring to FIGS. 1 and 3, the user may perform a predetermined treatment or surgery on the subject while observing an X-ray video provided via the display 172. In the course of the treatment or operation, the user, i.e., the hand of the user in particular, may frequently enter into a scanning region or field of view (FOV) into which X-rays are irradiated, thereby putting the user at risk of being exposed to X-ray radiation.

For this reason, the X-ray imaging apparatus 100 may use the filter unit 200 to minimize the dosage amount of X-rays to be irradiated toward the user, in order to reduce the risk of the user with respect to being exposed to X-ray radiation. An object that wants no X-ray irradiation, such as the user, is referred to herein as an uninterested object U.

The X-ray imaging apparatus 100 may set up a region on the subject, and may control the filtering unit 200 in order to control a dosage amount of X-rays to be irradiated toward the region. A process of setting up the region will be described below before description of the filtering unit 200.

Figure 4:
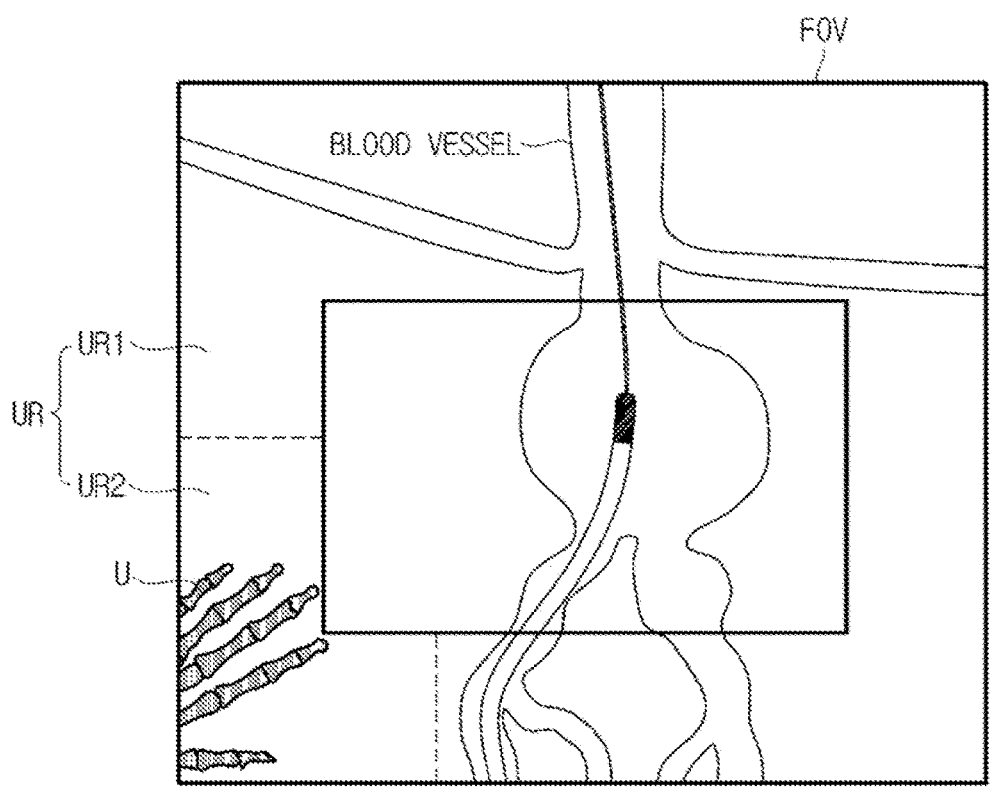
FIG. 4 illustrates a detection of an uninterested object by an X-ray imaging apparatus, according to an exemplary embodiment.
Figure 5:
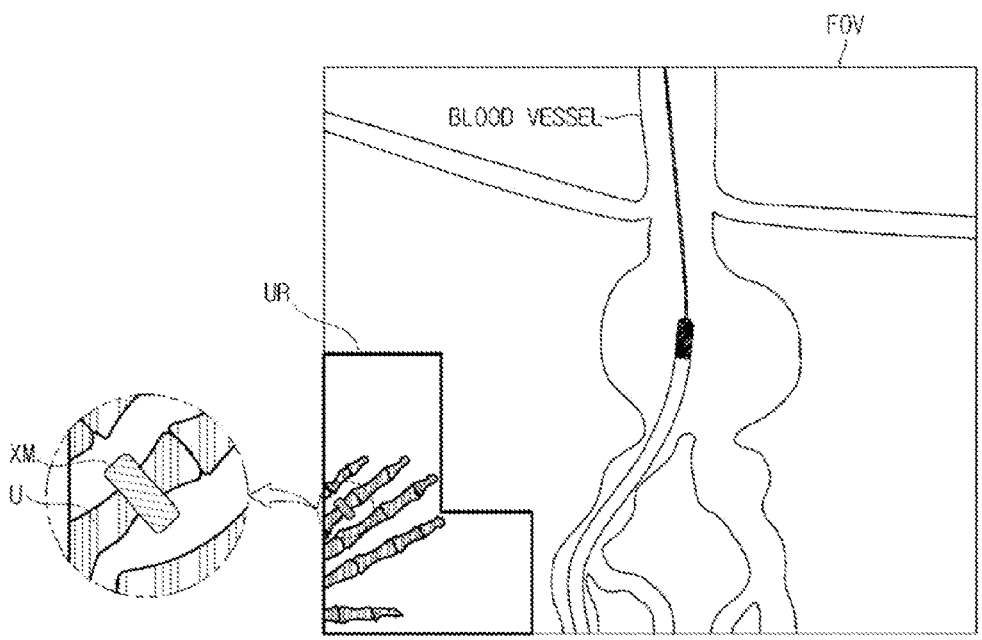
FIG. 5 illustrates a detection of an uninterested object by an X-ray imaging apparatus, according to another exemplary embodiment.
Figure 6:
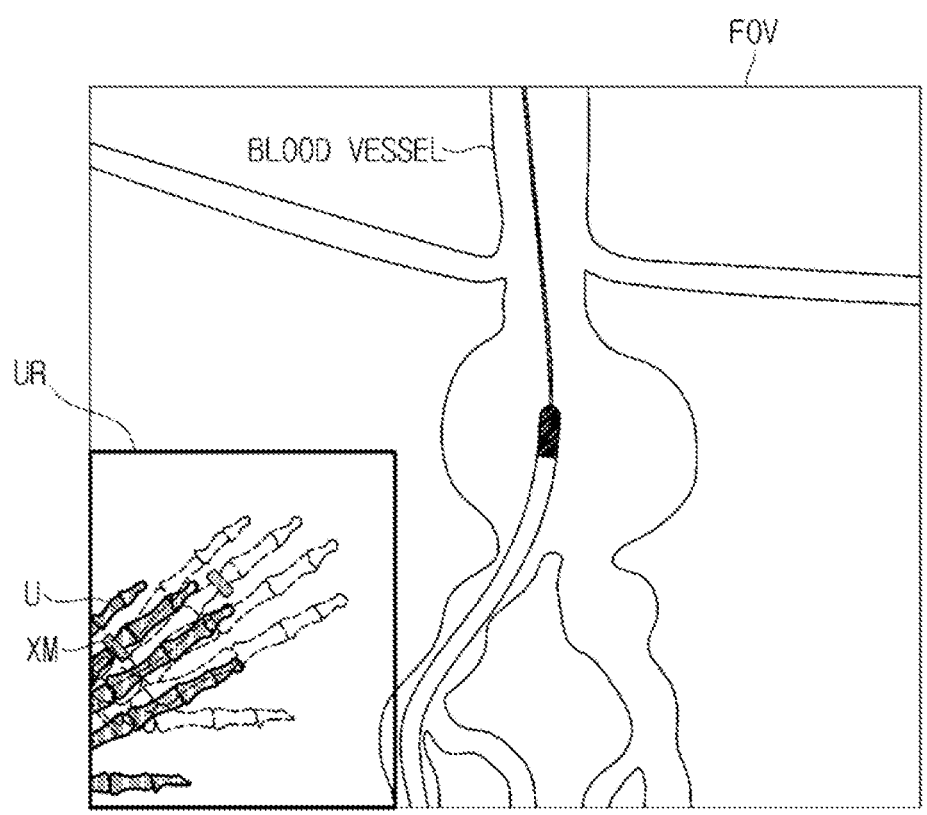
FIG. 6 illustrates an establishment of an uninterested region by an X-ray imaging apparatus, according to an exemplary embodiment.

FIG. 4 illustrates a detection of an uninterested object by an X-ray imaging apparatus, according to an exemplary embodiment, FIG. 5 illustrates a detection of an uninterested object by an X-ray imaging apparatus, according to another exemplary embodiment, and FIG. 6 illustrates an establishment of an uninterested region by an X-ray imaging apparatus, according to another exemplary embodiment.

Referring to FIGS. 3, 4, 5, and 6, the control processor 180 may be configured to set up a region on the subject ob.

The control processor 180 may be further configured to establish a scanning region FOV and an uninterested region UR.

The scanning region FOV is a region for which an X-ray image is obtained. To obtain the X-ray image, X-rays are irradiated into the scanning region FOV. The scanning region FOV may be set up by the user in person, or by the control processor 180. For example, the control processor 180 may automatically set up the scanning region FOV on the subject ob, or may sequentially change the established scanning region FOV, according to a predetermined protocol.

Within the scanning region FOV, the uninterested region UR may be set up. The uninterested region UR is a part of the scanning region FOV, which contains the uninterested object U, and thus the control processor 180 may set up the uninterested region UR to include the uninterested object U.

The control processor 180 may detect the uninterested object from the X-ray image created by the image processor 150 in order to set up the uninterested region UR.

As shown in FIG. 4, the uninterested object U has different characteristics from the subject ob. The control processor 180 may store the characteristics of the uninterested object U in advance, and may detect the uninterested object U from an X-ray image by using the stored characteristics of the uninterested object U.

The characteristics of the uninterested object U may include at least one from among a shape, a size, a pattern, a movement property, and an X-ray absorption property of the uninterested object U. For example, a feature of the user's hand, as shown in FIG. 4, and an X-ray absorption property may be stored, based on which the uninterested object may be detected.

The control processor 180 may detect the uninterested object U by using a marker formed on the uninterested object U.

Referring to FIG. 5, the control processor 180 may search for a marker which includes a particular pattern in the X-ray image in order to detect the uninterested object U. For this purpose, the marker is formed on the uninterested object U.

The marker formed on the uninterested object U has a particular pattern in the X-ray image, whose transmittance is different from that of the subject or uninterested object. For example, the marker may include a substance which has a higher X-ray penetration characteristic than a surrounding area, or a radio-opaque substance.

The marker may be formed to be easily mounted on the uninterested object U. In an exemplary embodiment, the marker may have the form of a patch to be attached to the uninterested object U. In another exemplary embodiment, the uninterested object U may have a wearable form, e.g., a glove or ring form.

As shown in FIG. 5, the marker may be a dosimeter XM which is intended to be worn around a finger of the user for use. The dosimeter XM is a device that is configured for detecting an exposure of the user to radiation, and specifically, to be worn around a finger of the user for measuring a dosage amount of X-rays irradiated to the user, thus detecting a level of exposure of the user to radiation.

The dosimeter XM has a certain shape and pattern in the X-ray image. Thus, the control processor 180 may store the pattern of the dosimeter XM, and search the X-ray image for a region that matches the stored pattern in order to detect the dosimeter XM. Further, the control processor 180 may detect the uninterested object U that comes into contact with the dosimeter XM and forms a region.

The marker attached to the uninterested object U may include a magnetic field generator (see IM of FIG. 20) as will be described below.

Once the uninterested object U is detected, the control processor 180 may set up an uninterested region UR. The uninterested region UR may be set up by taking into account characteristics of the uninterested object U, such as any of a location, a size, a shape, etc., of the uninterested object U.

The uninterested region UR may be set up in an asymmetrical shape. The uninterested region UR formed in the symmetrical shape so as to reduce exposure of the uninterested object U to radiation may lead to degradation in an overall quality of the X-ray image, thereby making it difficult to provide sufficient information to the user. Hence, the control processor 180 may set up the uninterested region to have an asymmetrical shape based on the shape of the uninterested object U.

For example, if the uninterested region UR is formed to have a symmetrical shape as shown in FIG. 4, not only a second region UR2 which contains the uninterested object U but also a first region UR1 which does not contain the uninterested object may be set up as the uninterested region UR, and thus a lower dosage amount of X-rays may be irradiated even into the first region UR1. This degrades the quality of not only the second region UR2 but the first region UR1 as well, thus making it difficult to provide sufficient information for the user.

Accordingly, the control processor 180 may set up the uninterested region UR asymmetrically based on the shape of the uninterested object U, as shown in FIG. 5, and thus provide sufficient information to the user while reducing the exposure of the user to radiation.

The shape of the uninterested region UR may be determined based on the feature of the detected uninterested object U, and/or based on the shape of a filtering region formed by an uninterested region filter 210.

Alternatively, the uninterested region R may be set up by taking into account the movement of the uninterested object U. For example, the control processor 180 may set up the uninterested region UR to be larger if the uninterested object U makes a relatively large movement, and smaller if the uninterested object U makes a relatively small movement.

Since the uninterested object U continues to move, it is required that movements of the uninterested object U be predicted and that the uninterested region UR be set up by taking into account the predicted movements of the uninterested object U, in order to reduce the exposure of the uninterested object U to radiation.

In particular, the control processor 180 may calculate the movement direction and speed of the uninterested object U by tracking the uninterested object U in the X-ray image. Based on the calculated movement speed and direction of the uninterested object U, the control processor 180 may predict the next movement of the uninterested object U, and then set up the uninterested region U to include a region into which the uninterested object U is predicted to move.

For example, if the uninterested object U is moving toward the center of the screen at a certain speed, the control processor 180 may predict that the uninterested object U will move into a dashed region of FIG. 6, and set up the uninterested region UR to include the dashed region.

Figure 7:
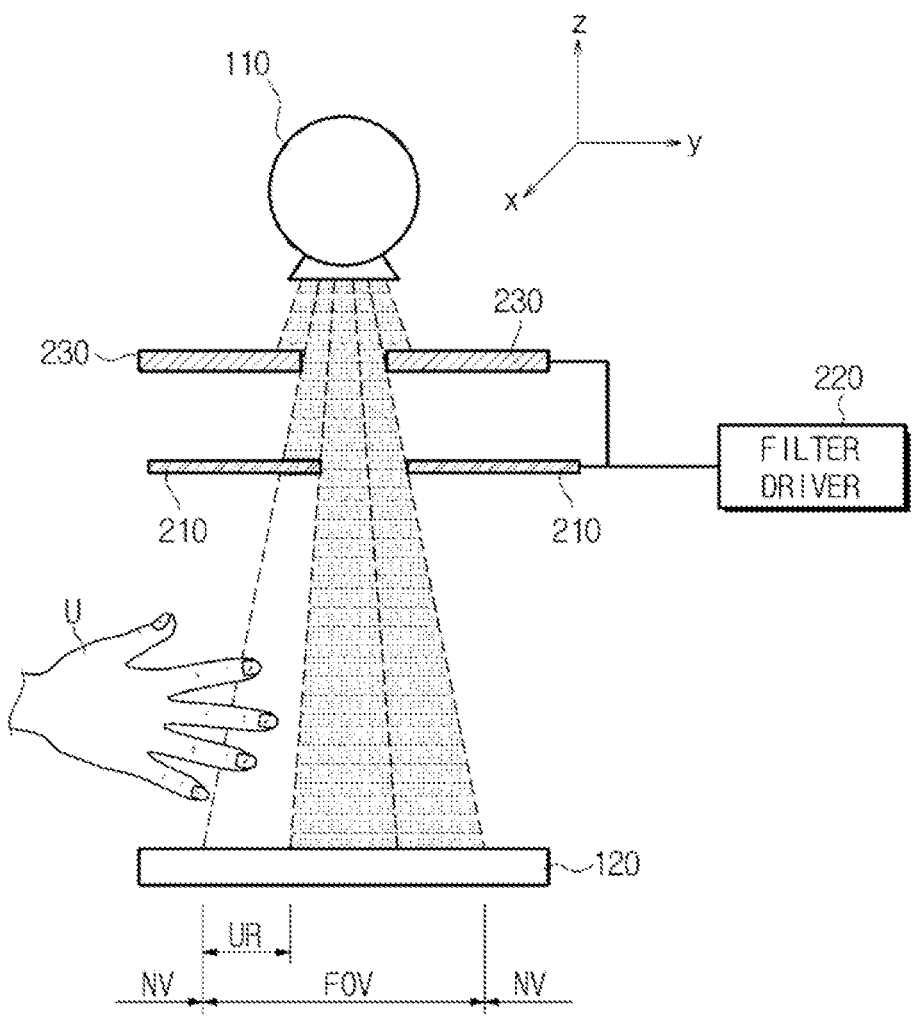
FIG. 7 is a schematic cross-sectional view of a filtering unit, according to an exemplary embodiment.
Figure 8:
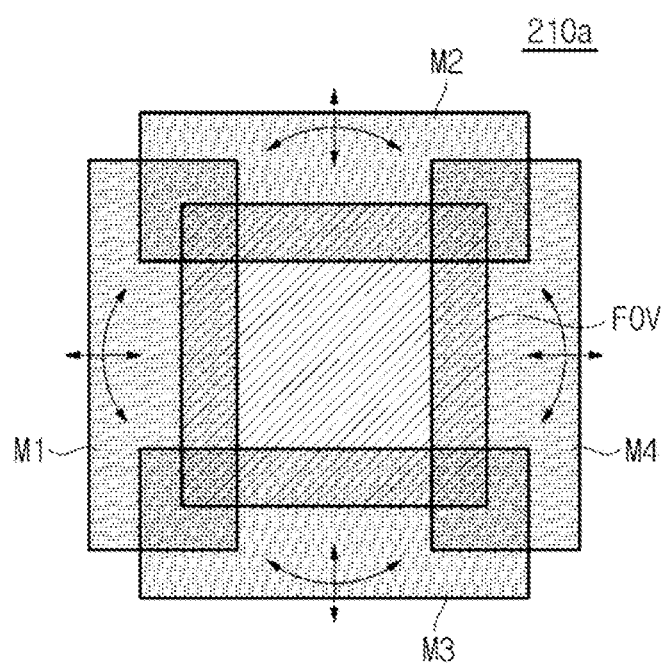
FIG. 8 is a schematic plane view of a variable uninterested region filter, according to an exemplary embodiment.
Figure 9:
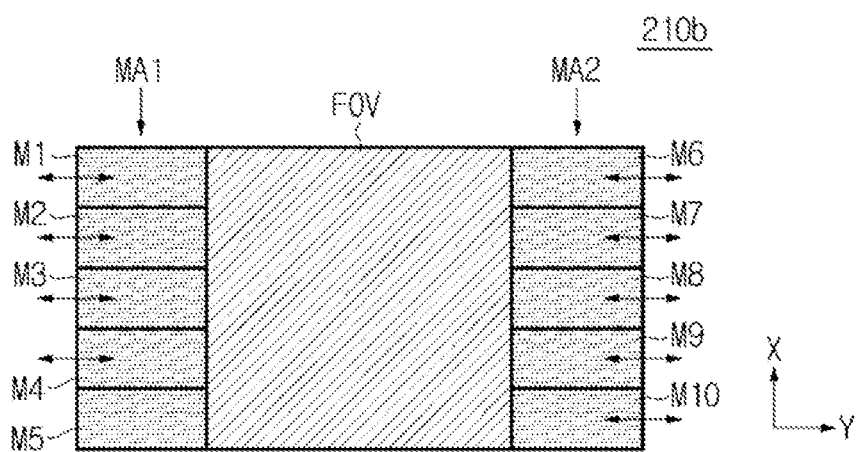
FIG. 9 is a schematic plane view of a variable uninterested region filter, according to another exemplary embodiment.
Figure 10:
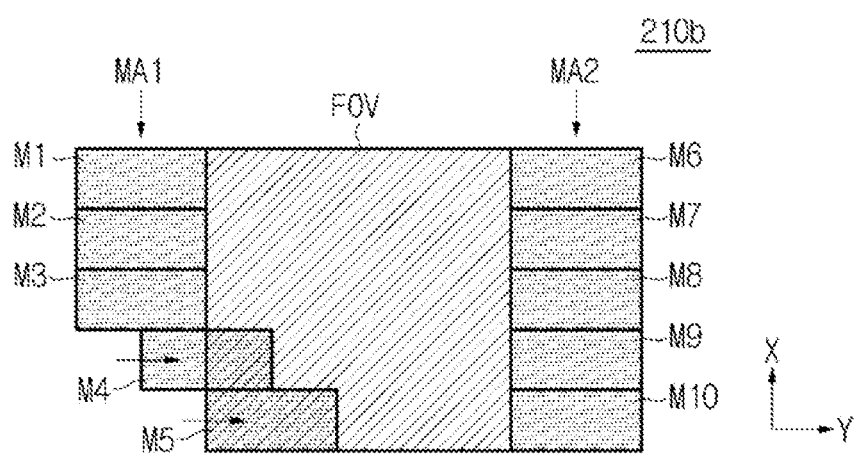
FIG. 10 illustrates a view for describing an operation of the variable uninterested region filter shown in FIG. 8.
Figure 11:
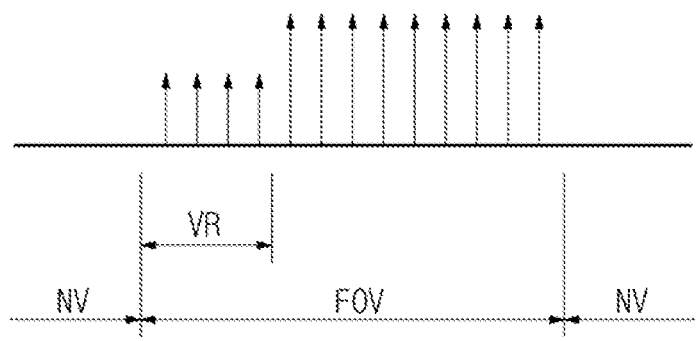
FIG. 11 schematically illustrates doses of X-rays incident upon an X-ray detector.

FIG. 7 is a schematic cross-sectional view of a filtering unit, according to an exemplary embodiment, FIG. 8 is a schematic plane view of a variable uninterested region filter, according to an exemplary embodiment, FIG. 9 is a schematic plane view of a variable uninterested region filter, according to another exemplary embodiment, FIG. 10 illustrates a view for describing an operation of the variable uninterested region filter shown in FIG. 8, and FIG. 11 schematically illustrates doses of X-rays incident upon an X-ray detector.

Referring to FIGS. 2 and 7, the filtering unit 200 may be arranged between the X-ray source 110 and the X-ray detector 120 and configured for controlling the dosage amount of X-rays to be irradiated toward the subject ob.

The filtering unit 200 may be equipped in the X-ray generating assembly 107 together with the X-ray source 110, but is not limited thereto. For example, the filtering unit 200 may be arranged on the table 109 on which the subject ob lies.

Specifically, the filtering unit 200 may include a collimator 230 configured for adjusting the scanning region FOV, an uninterested region filter 210 configured for filtering X-rays irradiated into the uninterested region UR, and a filter driver 220 configured for driving the filter.

The collimator 230 may be placed in the direction of X-ray irradiation, which corresponds to the forward direction of the X-ray source 110, for adjusting the direction and range for X-ray irradiation. The collimator 230 may be formed of a substance that absorbs or blocks X-rays, such as lead (Pb) or tungsten (W). In this regard, as shown in FIGS. 7 and 11, the collimator 230 may absorb or block X-rays irradiated toward a region NV other than the scanning region FOV.

Furthermore, the collimator 230 may form the scanning region by being moved by the filter driver 220 on the x-y plane or along the z-axis. Movement of the collimator 230 on the x-y plane leads to a corresponding change in position of the scanning region into which X-rays are to be irradiated, and movement of the collimator 230 along the z-axis may lead to a corresponding change in size of the scanning region.

The uninterested region filter 210 may be arranged between the collimator 230 and the X-ray detector 120, but is not limited thereto. For example, the uninterested region filter 210 may be placed between the X-ray source 110 and the collimator 230.

Furthermore, the uninterested region filter 210 may be formed of a substance that reduces X-rays in order to facilitate the filtering of X-rays irradiated to the uninterested region UR from the X-ray source 110.

The X-rays irradiated from the X-ray source 110 to the uninterested region UR are filtered by the uninterested region filter 210. Accordingly, as shown in FIGS. 7 and 11, a lower dosage amount of X-rays may be incident onto the uninterested region UR, as compared to a remaining portion of the scanning region FOV.

Since X-rays are incident onto the uninterested region UR, though it is a lower dose of X-rays, the X-ray imaging apparatus 100 may reduce the risk of the uninterested object U being exposed to radiation while providing the X-ray video with respect to the entire scanning region FOV.

The uninterested region filter 210 may form a filtering region that corresponds to the uninterested region UR by being moved by the filter driver 220 on the x-y plane or along the z-axis.

The uninterested region filter 210 may be implemented as a variable filter which is configured to variably change the shape of the filtering region.

The variable uninterested region filter 210 may include a plurality of movable masks. Each mask may be formed of a substance that reduces X-rays, and each of the plurality of masks may be moved by the filter driver 220 to form a filtering region in a variable shape.

FIG. 8 illustrates an uninterested region filter which has a wedge shape. Referring to FIG. 8, an uninterested region filter 210a in accordance with an exemplary embodiment may include a plurality of masks M1, M2, M3, and M4.

The masks M1, M2, M3, and M4 may be moved by the filter driver 220 to form a filtering region in a shape that corresponds to the uninterested region UR. A mask may be pivotably moved, or moved in the upward, downward, leftward, or rightward direction on the x-y plane without interference of another mask.

For freedom of movement among the masks, the plurality of masks M1, M2, M3, and M4 may be arranged in multiple layers. For example, first and fourth masks M1 and M4, which are oriented to be parallel to the y-axis, may be arranged in the first layer, and second and third masks M2 and M3, which are oriented to be perpendicular to the y-axis, may be arranged in the second layer.

In another example, each of the plurality of masks M1, M2, M3, and M4 may be arranged in a different layer. Specifically, the first mask M1 may be arranged in the first layer, the second mask M2 may be arranged in the second layer, the third mask M3 may be arranged in the third layer, and the fourth mask M4 may be arranged in the fourth layer.

FIG. 9 shows an uninterested region filter 210b in a multi-leaf shape. As shown in FIG. 9, a plurality of masks M1 to M10 of the uninterested region filter 210b may be arranged in the same layer.

Specifically, two mask arrays MA1, MA2 may be arranged in parallel to the y-axis. Each mask array MA1, MA2 may have a respective plurality of masks, i.e., mask array MA1 may include M1, M2, M3, M4, and M5, and mask array MA2 may include M6, M7, M8, M9, and M10, and the two mask arrays MA1 and MA2 may be arranged to be adjacent to each other.

The masks M1 to M10 may be moved by the filter driver 220 in a direction that is parallel to the x-axis, in order to form a filtering region in a shape that corresponds to the uninterested region UR.

The filter driver 220 may drive the collimator 230 and the uninterested region filter 210 under the control of the control processor 180. For this, the filter driver 220 may include mechanical structures, such as an actuator configured for producing a dynamic force and a gear configured for delivering the dynamic force produced by the actuator.

In particular, the filter driver 220 may move the collimator 230 based on the scanning area FOV set up by the control processor 180

The filter driver 220 may also move the uninterested region filter 210 to the uninterested region UR, or drive the uninterested region filter 210 to form a filtering region that corresponds to the shape of the uninterested region UR, under the control of the control processor 180.

For example, once the uninterested region UR is established as shown in FIG. 5, the filter driver 220 may move the fourth and fifth masks M4 and M5 into the scanning region FOV, in order to form a filtering region of the uninterested region filter 210b so as to have a shape that corresponds to the uninterested region UR.

Figure 12:
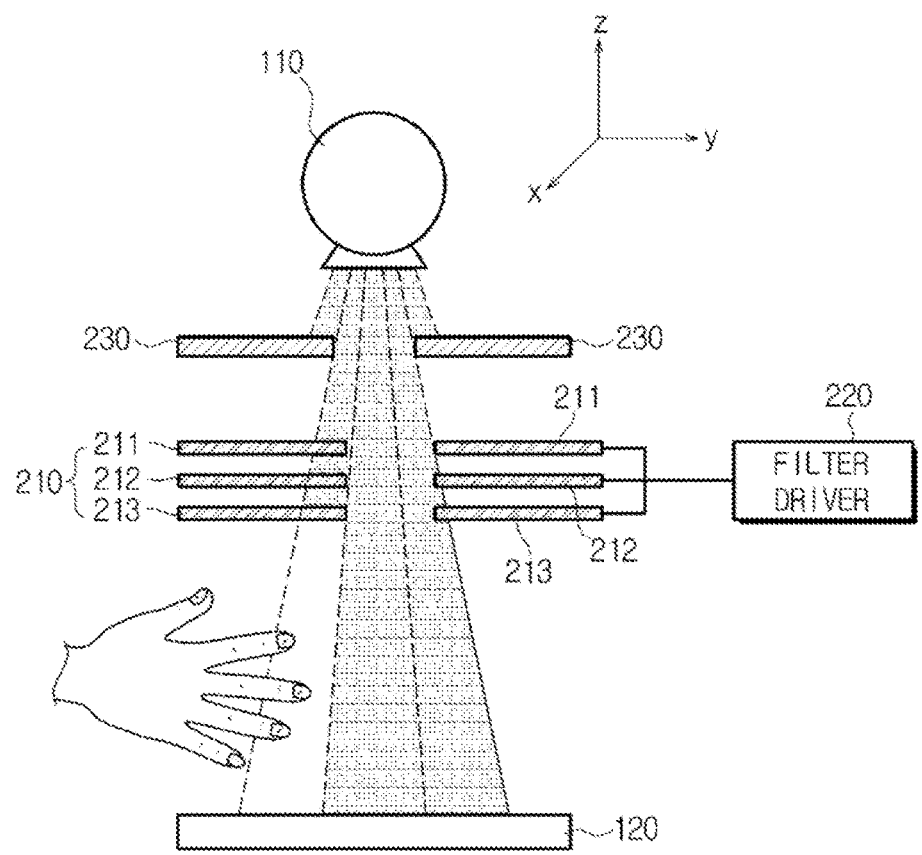
FIG. 12 is a schematic cross-sectional view of a filtering unit which has a plurality of uninterested region filters.

FIG. 12 is a schematic cross-sectional view of a filtering unit which has a plurality of uninterested region filters. Although the filtering unit 200 of FIG. 7 has the single uninterested region filter 210, the filtering unit 200 may include multiple uninterested region filters 211, 212, 213, as shown in FIG. 12.

The multiple uninterested region filters 211, 212, 213 may be formed of the same filtration material but have different thicknesses, or formed of different filtration materials and have different thicknesses, or formed of different filtration materials but have the same thickness, or formed of the same filtration material and have the same thickness.

The multiple uninterested region filters 211, 212, 213 may be arranged in multiple layers on the z-axis, and may each be driven by the filter driver 220. All or some of the multiple uninterested region filters 211, 212, 213 may be variable filters which are configured to form variable shapes of filtering regions.

The control processor 180 may combine filtering regions of the multiple uninterested region filters 211, 212, 213 in order to form a filtering region that corresponds to the uninterested region UR.

While the filtering unit 200 incorporates the collimator 230 in the exemplary embodiment of FIG. 5, the collimator 230 may be implemented as a separate component.

In addition, the image processor 150 and the control processor 180 are separate components in the exemplary embodiment of FIG. 2, but they may be implemented in a single processor. If the image processor 150 and the control processor 180 are implemented in a single processor, image processing and control processing may be performed in parallel.

The image processor 150 may restore an X-ray image of the uninterested region UR. Since the X-rays irradiated to the uninterested region UR are filtered, a lower dosage amount of X-rays are irradiated to the uninterested region UR, as compared to a remaining portion of the scanning region. Accordingly, a need exists for restoring an image of the uninterested region UR.

There are no limitations on how to restore an image of the uninterested region UR. For example, the image processor 150 may restore an image of the uninterested region UR by using an X-ray image which is obtained before the uninterested region UR is established.

As such, by restoring an image of the uninterested region UR using an X-ray image that was previously obtained, the image processor 150 may obtain the image of the uninterested region UR with a relatively strong signal-to-noise (SNR) ratio as an image of a region into which a higher dosage amount of X-rays are irradiated.

The image processor 150 may also execute an image equalization algorithm in order to match the brightness and contrast between the restored images of the uninterested region UR and the remaining portion of the scanning region.

Figure 13:
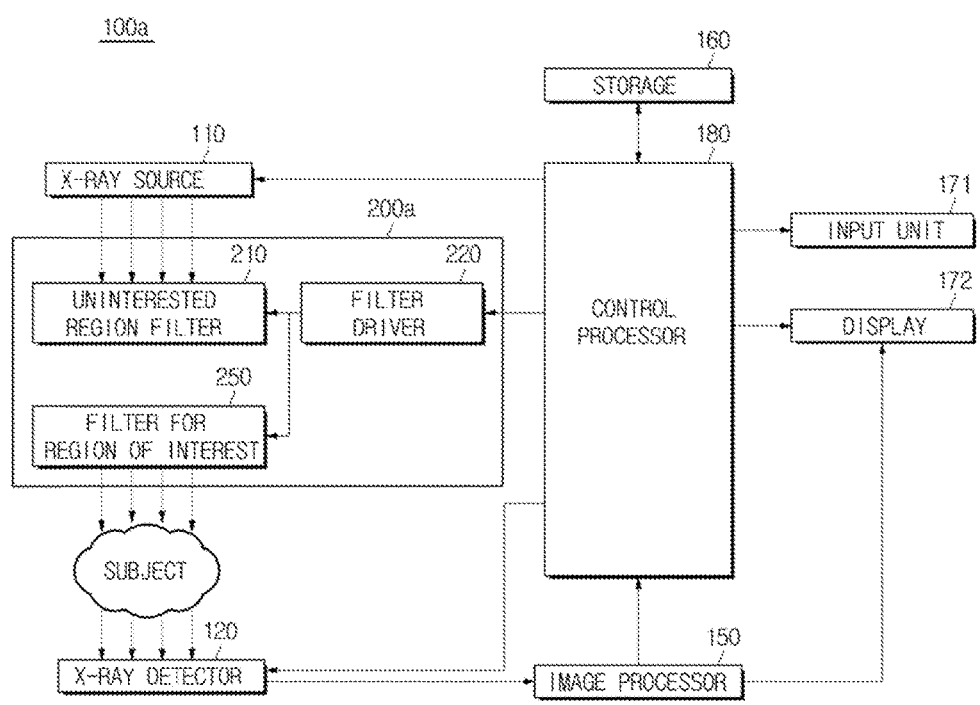
FIG. 13 is a control block diagram of an X-ray imaging apparatus, according to another exemplary embodiment.
Figure 14:
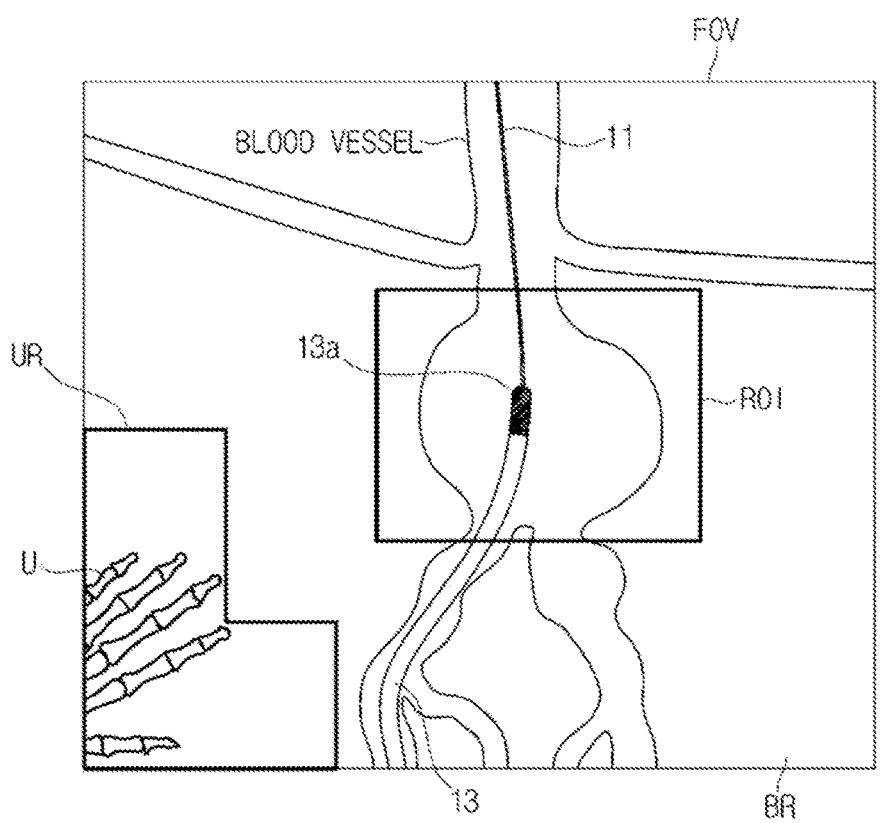
FIG. 14 illustrates a view for describing an establishment of a region of interest.
Figure 15:
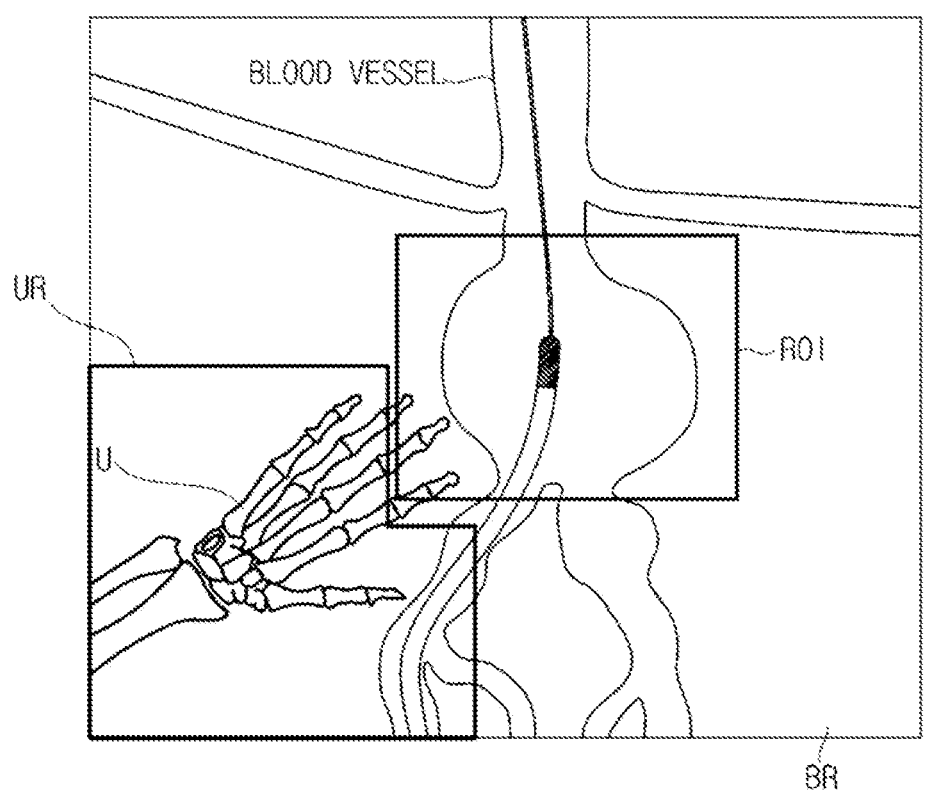
FIG. 15 illustrates a view for describing an establishment of a region of interest and an uninterested region, according to an exemplary embodiment.
Figure 16:
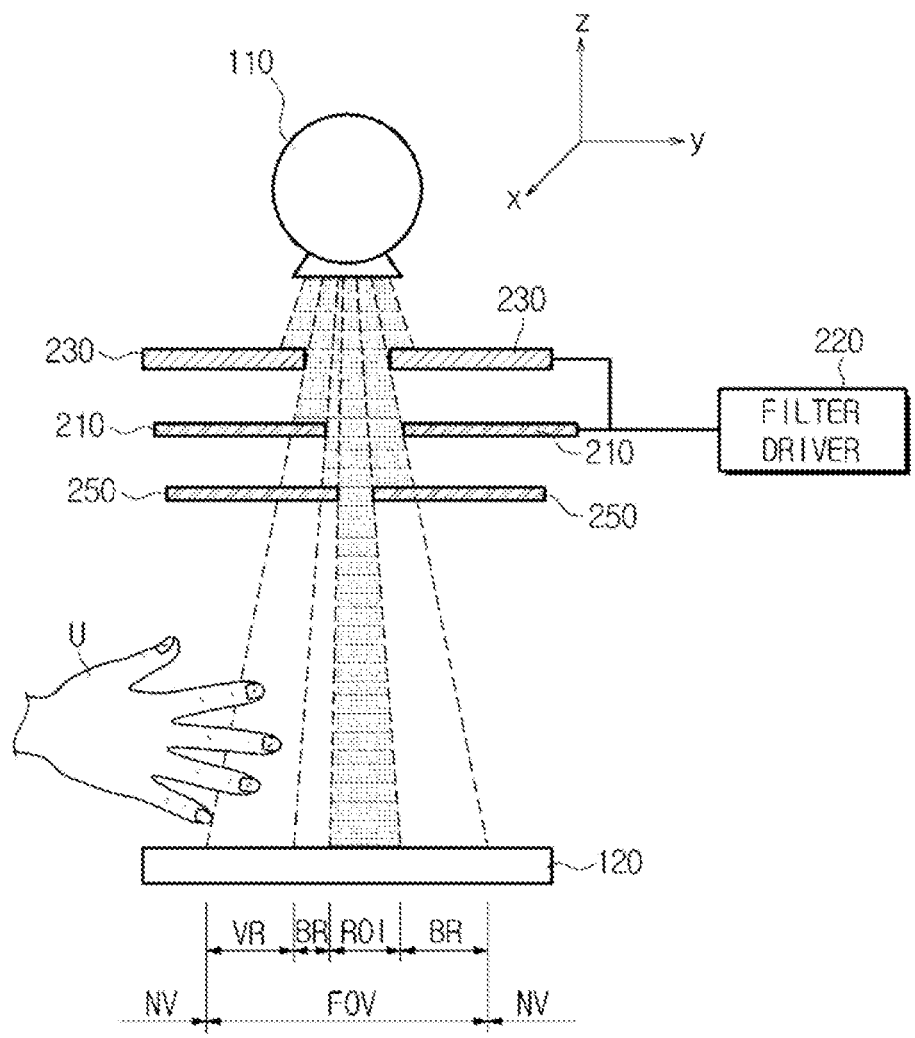
FIG. 16 illustrates a filtering unit of an X-ray imaging apparatus, according to an exemplary embodiment.
Figure 17:
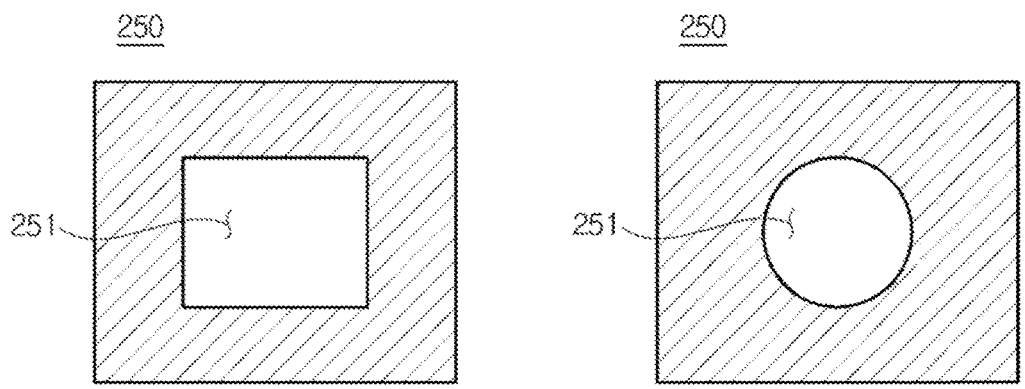
FIG. 17 schematically illustrates a filter for a region of interest.
Figure 18:
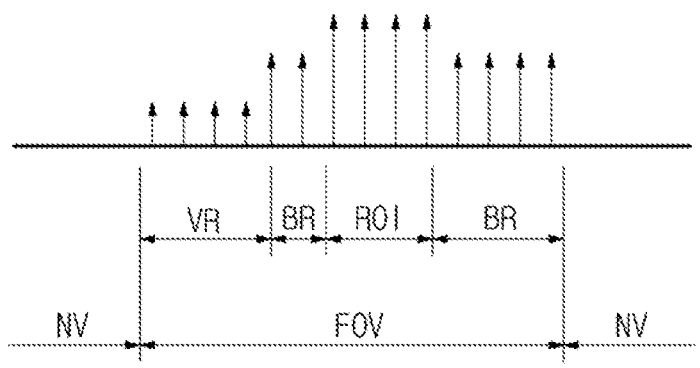
FIG. 18 schematically illustrates doses of X-rays incident on a scanning region.

FIG. 13 is a control block diagram of an X-ray imaging apparatus, according to another exemplary embodiment, FIG. 14 illustrates a view for describing an establishment of a region of interest, FIG. 15 illustrates a view for describing an establishment of a region of interest and an uninterested region, according to an exemplary embodiment, FIG. 16 schematically illustrates a filtering unit of an X-ray imaging apparatus, according to an exemplary embodiment, FIG. 17 schematically illustrates a filter for region of interest, and FIG. 18 schematically illustrates doses of X-rays incident onto a scanning region.

An X-ray imaging apparatus 100a in accordance with another exemplary embodiment will now be described in connection with FIGS. 13 to 18. The same components as in the X-ray imaging apparatus 100 have the same reference numerals, and the detailed description of them will be omitted herein. Unless stated otherwise, the components of the X-ray imaging apparatus 100a may have the same respective functions and perform the same respective operations as the corresponding components of the X-ray imaging apparatus 100.

Referring to FIGS. 13 and 14, the X-ray imaging apparatus 100a may include an X-ray source 110 configured for irradiating X-rays, a filtering unit (also referred to herein as a "filter") 200a configured for controlling a dose (i.e., a dosage amount) of X-rays to be irradiated from the X-ray source 110, an X-ray detector 120 configured for detecting X-rays in order to obtain frame data, an image processor 150 configured for creating an X-ray image and/or an X-ray video based on the frame data, and a control processor 180 configured for controlling the components of the X-ray imaging apparatus 100a.

As described above, X-rays are constantly irradiated to the subject ob in order to facilitate a creation of an X-ray video, so there is a higher risk of the subject ob being exposed to radiation. Accordingly, the X-ray imaging apparatus 100a may minimize the exposure of the subject ob to radiation by establishing a region of interest ROI, for which a high quality of X-ray video with a low SNR is required, within the scanning region FOV, and irradiating a lower dosage amount of X-rays to a background region BR other than the region of interest ROI. A methodology relating to how to establish a region of interest ROI will now be described in detail.

The scanning region FOV may be divided into a region of interest ROI for which a clear X-ray video is required, an uninterested region UR which contains an uninterested object U, and a background region BR which includes the remaining portion of the scanning region, i.e., which excludes the region of interest ROI and the uninterested region UR.

The region of interest ROI may be set up to contain an object of interest. The object of interest is an object that requires constant attention via an X-ray video, such as a treatment instrument used for the subject ob or a region for treatment. For example, in a case in which the X-ray imaging apparatus 100a is used in angiography, a treatment instrument, such as a guide wire, catheter, needle, balloon, stent, etc., needs close observation, so the treatment instrument may be the object of interest.

In the case in which the treatment instrument is set up to be an object of interest, a particular region of the subject ob, such as a stenosis, aneurysm, cancerous region, or the like, may be the object of interest.

The object of interest may be set up by the user, or determined according to a pre-stored protocol. For example, if some information is received, for example, via user input, regarding any of the type of a treatment instrument, a type of treatment, a region for treatment, whether to inject contrast media, etc., the control processor 180 may select the object of interest based on the received information.

Once the object of interest is selected, the control processor 180 may detect an object of interest in the X-ray image. The object of interest may be detected based on pre-stored characteristics of the object of interest. The characteristics of the object of interest may include at least one from among a shape, an X-ray absorption property, and a movement property of the object of interest.

Once the object of interest is detected, the control processor 180 may set up a region of interest ROI by using the object of interest. In particular, the scanning region FOV may be divided by the control processor 180 into a region of interest ROI and a background region (BR) other than the region of interest ROI.

The region of interest ROI may be established to include the object of interest based on a position, a shape, and a size of the object of interest.

Furthermore, the region of interest ROI may be established by reflecting the movement of the object of interest. In particular, the control processor 180 may set up the region of interest to be relatively wide if the object of interest makes a relatively large movement. Also, if an uncertainty about the movement of the object of interest is great, the region of interest ROI may be set up to be relatively wide.

Furthermore, the region of interest ROI may be established by reflecting the predicted movement of the object of interest. In particular, the control processor 180 may calculate a movement direction and a speed of the object of interest by tracking the movement of the object of interest. The control processor 180 may predict the movement of the object of interest by using the calculated movement direction and speed, and set up a region of interest ROI to include a region into which the object of interest is predicted to move.

A specific exemplary embodiment which relates to how to establish a region of interest ROI will be described in connection with FIG. 14. In FIG. 14, a circumstance in which a stent is inserted into a blood vessel by using angiography is taken as an example. A stent 13a is inserted into a blood vessel in order to prevent obstruction of the blood vessel, and the stent 13a may have a kind of mesh-like form. The stent 13a is inserted into the blood vessel in a folded state with the aid of a stent device 13 in the form of a long tube with an end at which the stent 13a is mounted, and is unfolded in the mesh-like form at a desired location.

In order to cause the stent device 13 to be inserted into the blood vessel, a guide wire 11 is inserted first. The stent device 13 is inserted into the blood vessel along the guide wire 11, and unfolded at the blocked point in the blood vessel.

The control processor 180 may set the stent device 13, the stent 13a in particular on the tip of the stent device 13, with respect to the object of interest while the stent device 13 is being inserted, and set a region which includes the object of interest, i.e., the stent 13a, to a region of interest ROI.

The object of interest may be changed during the treatment. For example, while the guide wire 11 is being inserted, the guide wire 11 or the tip of the guide wire 11 may be the object of interest, and while a catheter is being inserted in order to inject contrast media into the blood vessel, the catheter or the tip of the catheter may be the object of interest.

The control processor 180 may establish an uninterested region UR after setting up the region of interest ROI. Setting up the uninterested region UR first might lead to a reduction of the dosage amount of X-rays to be irradiated to a region of interest. Accordingly, the control processor 180 may first establish the region of interest ROI, and then establish an uninterested region UR so as not to overlap the region of interest ROI.

For example, the control processor 180 may set up the uninterested region UR just within the background region BR, as shown in FIG. 15, in order to prevent the region of interest ROI and the uninterested region UR from overlapping each other.

Referring to FIG. 16, the filtering unit 200a may further include a filter for region of interest (also referred to herein as a "region-of-interest filter") 250. The filter for region of interest 250 may filter X-rays irradiated to the background region BR.

The filter for region of interest 250 may be arranged between the uninterested region filter 210 and the X-ray detector 120, as shown in FIG. 16, but is not limited thereto. For example, the position of the filter for region of interest 250 may be interchanged with that of the uninterested region filter 210 or that of the collimator 230.

The uninterested region filter 250 may be formed of a substance that reduces X-rays, in order to facilitate the filtering X-rays irradiated to the background region BR from the X-ray source 110. As the dosage amount of X-rays irradiated by the filter for region of interest 250 to the background region BR is reduced, the risk of the subject being exposed to radiation decreases.

The filter for region of interest 250 may be implemented as a variable filter which is configured to variably change the filtering region, or as a static filter which is configured to form a fixed shape for the filtering region.

As the region of interest ROI is surrounded by the background region BR, the filter for region of interest 250 may have a fixed shape with an empty center, as shown in FIG. 17.

In particular, the filter for region of interest 250 may have a shape with a polygonal opening 251, such as a rectangular ring as illustrated on the left side of FIG. 17, or a circular ring as illustrated on the right side of FIG. 17. The shape of the opening 251 of the filter for region of interest 250 may vary based on a feature of the region of interest ROI.

The filter for region of interest 250 may be moved by the filter driver 220 on the x-y plane or along the z-axis. In particular, the filter for region of interest 250 may be moved across the x-y plane based on the location of the region of interest ROI, or along the z-axis based on the size of the region of interest ROI.

For example, as the size of the region of interest ROI increases, the filter for region of interest 250 may be moved in the direction toward the X-ray detector 120, and as the size of the region of interest decreases, the filter for region of interest 250 may be moved in the direction toward the X-ray source 110.

The filter driver 220 may drive the collimator 230 such that X-rays are irradiated only to the scanning area FOV, under the control of the control processor 180. The filter driver 220 may drive the uninterested region filter 210 in order to form a filtering region that corresponds to the uninterested region UR, under the control of the control processor 180. The filter driver 220 may also drive the filter for region of interest 250 to form a filtering region that corresponds to the background region BR, under the control of the control processor 180.

As such, as the collimator 230, the uninterested region filter 210, and the filter for region of interest 250 are moved for an established region, the X-rays irradiated from the X-ray source 110 may sequentially propagate through the collimator 230, the uninterested region filter 210, and the filter for region of interest 250 to the subject ob, as shown in FIGS. 16 and 18.

In particular, since X-rays irradiated toward the other region NV, i.e., the region that is situated outside of the scanning region FOV, are absorbed or blocked by the collimator 230, there are no X-rays that successfully reach the other region NV, as shown in FIG. 18.

X-rays that propagate through the collimator 230 toward the uninterested region UR may be filtered by the uninterested region filter 210, and thus the dosage amount of the X-rays may be reduced.

The X-rays that propagate through the uninterested region filter 210 may further be filtered by the filter for region of interest 250, resulting in a reduction of the dosage amount of X-rays irradiated toward the background region.

In this aspect, the X-rays to be irradiated toward the background region BR are filtered by the filter for region of interest 250 and then are incident on the background region BR, and as a result, a lower dosage amount of X-rays may be incident on the background region BR than for the region of interest ROI, as shown in FIG. 18.

Furthermore, since the X-rays to be irradiated toward the uninterested region UR are filtered multiple times and then incident upon the uninterested region UR, a lower dosage amount of X-rays may be incident on the uninterested region UR than for the background region, as shown in FIG. 18.

Accordingly, the exposure of the subject ob to radiation may be reduced by irradiating a higher dosage amount of X-rays to the region of interest ROI while irradiating a lower dosage amount of X-rays to the background region BR, and may then be minimized by irradiating a lower dosage amount of X-rays to a region where the user who corresponds to the uninterested object U is positioned than to the background region BR.

In the meantime, the filtering unit 200a may include a plurality of filters for region of interest 250.

The plurality of filters for region of interest 250 may be arranged in multiple layers in order to facilitate controlling the shape of the region of interest ROI, and/or to facilitate controlling the dosage amount of X-rays to be irradiated to the background region BR.

As such, by controlling the dosage amount of X-rays variably for each region, the X-ray imaging apparatus 100a may provide the entire X-ray video to the user while reducing the exposure of the user and the subject ob to radiation.

Referring again to FIG. 13, the image processor 150 may be configured to restore an X-ray image not only for the uninterested region UR but also for the background region BR. As described above, as a low dosage amount of X-ray irradiation leads to obtaining an image with a relatively high SNR, the image processor 150 may restore the image of the background region BR by using an X-ray image obtained before an establishment of the background region BR.

The image processor 150 may also be configured to execute an image equalization algorithm in order to match the brightness and contrast of the restored images of the uninterested region UR and the background region BR with that the brightness and contrast of the image of the region of interest ROI.

As shown in FIG. 18, since different dosage amounts of X-rays are irradiated to the uninterested region UR and the background region BR, the image processor 150 may use different restoration methods or different equalization algorithms for the uninterested region UR and the background region BR.

Figure 19:
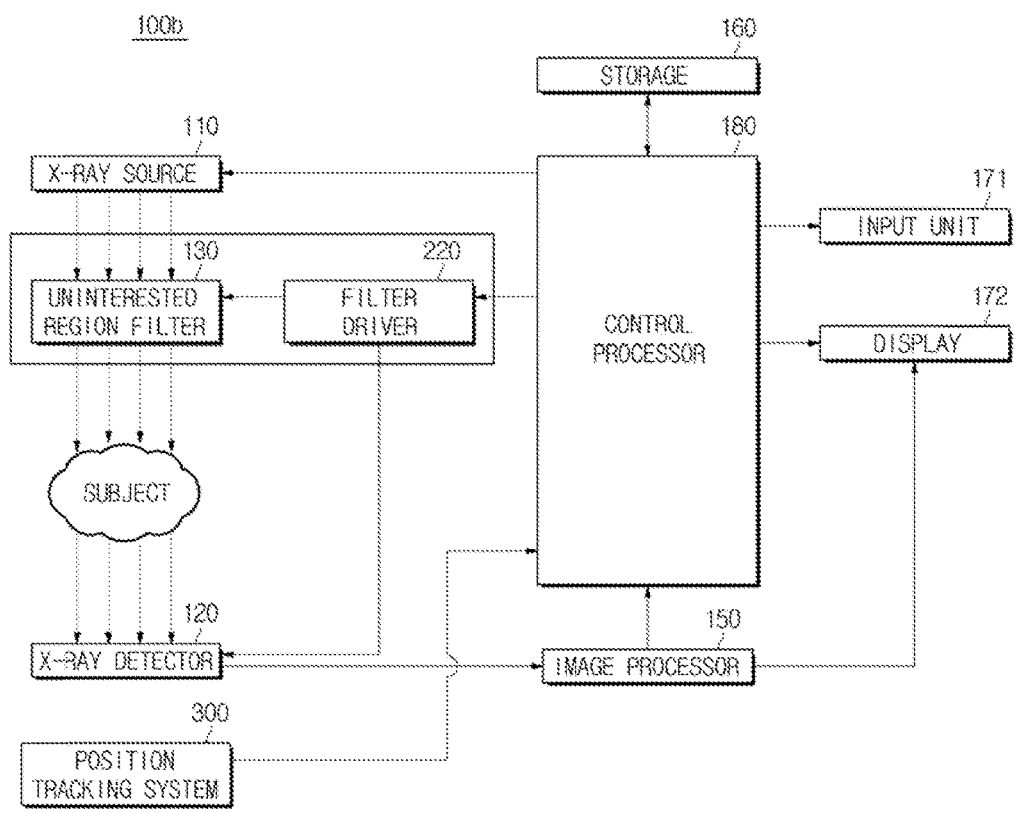
FIG. 19 is a block diagram of an X-ray imaging apparatus, according to another exemplary embodiment.
Figure 20:
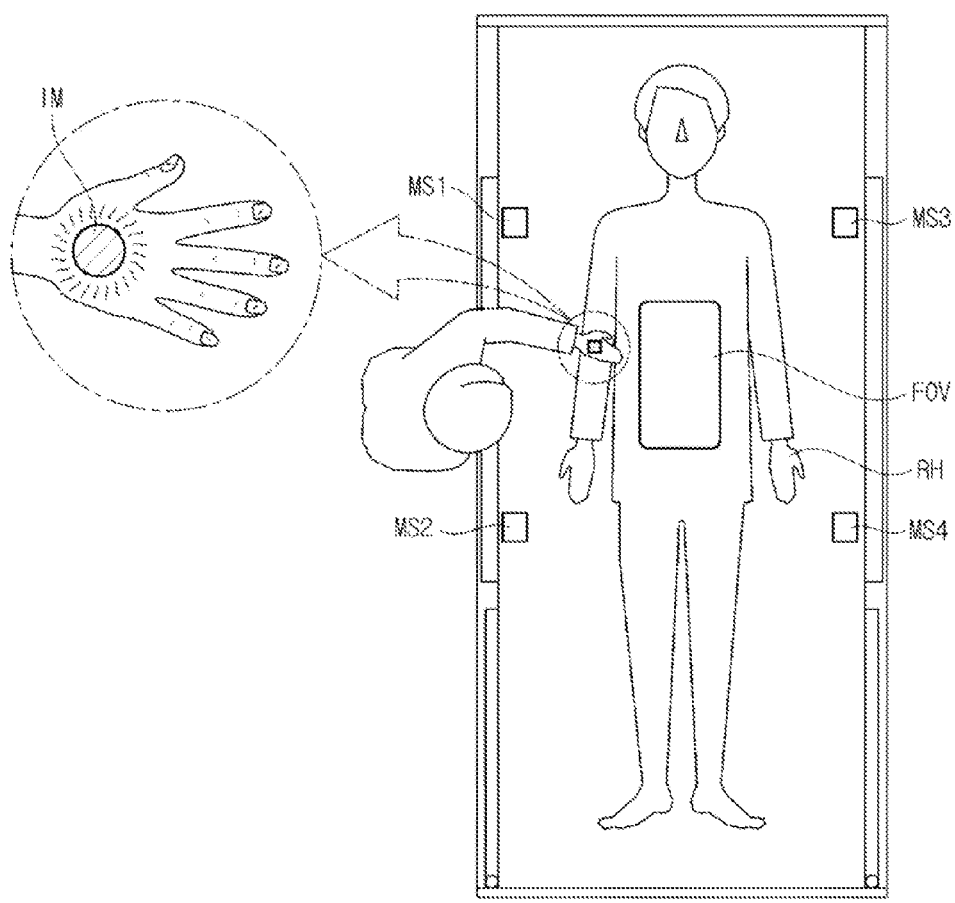
FIG. 20 illustrates a position tracking system which uses magnetic fields, according to an exemplary embodiment.
Figure 21:
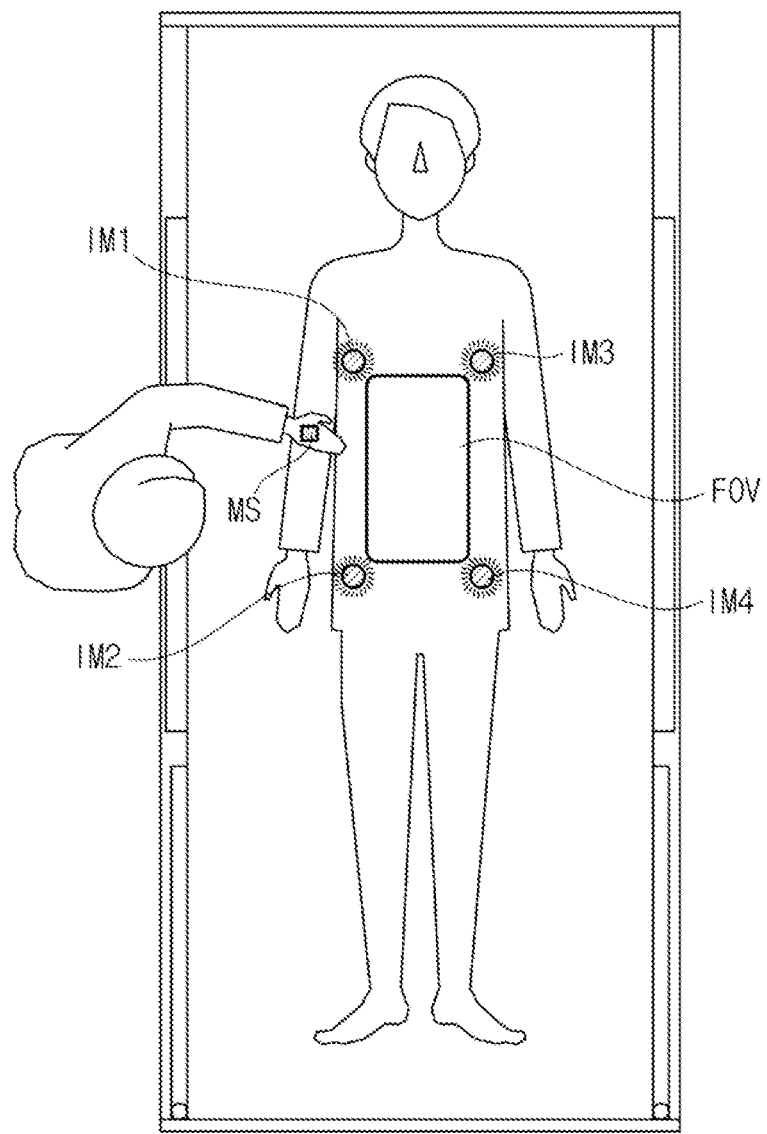
FIG. 21 illustrates a position tracking system which uses magnetic fields, according to another exemplary embodiment.

FIG. 19 is a block diagram of an X-ray imaging apparatus, according to another exemplary embodiment, FIG. 20 illustrates a position tracking system that uses magnetic fields, according to an exemplary embodiment, and FIG. 21 illustrates a position tracking system that uses magnetic fields, according to another exemplary embodiment.

An X-ray imaging apparatus 100b in accordance with another exemplary embodiment will now be described in connection with FIGS. 19, 20, and 21. The same components as in the X-ray imaging apparatus 100 have the same reference numerals, and the detailed description of them will be omitted herein. Unless stated otherwise, the components of the X-ray imaging apparatus 100b may have the same respective functions and perform the same respective operations as the corresponding components of the X-ray imaging apparatus 100.

FIG. 19 is a block diagram of an X-ray imaging apparatus, according to another exemplary embodiment.

Referring to FIG. 19, an X-ray imaging apparatus 100b in accordance with another exemplary embodiment may further include a position tracking system (also referred to herein as a "position tracking device") 300 which is configured for tracking the location of an uninterested object U.

As described above, once the uninterested region UR is established by detecting the uninterested object U from the X-ray image, the uninterested object U may be exposed to intense X-rays when entering into the scanning area FOV, thereby increasing the risk of the user being exposed to radiation.

Accordingly, the X-ray imaging apparatus 100b may use the position tracking system 300 to track the location of the uninterested object U, collect position information of the uninterested object U, and set up a part of the scanning region FOV into which the uninterested object U is expected to move to be an uninterested region UR in advance, based on the collected position information. The position information as herein used may refer to information obtained by tracking the location of the uninterested object U, including, for example, information about the location, movement, etc., of the uninterested object U.

In an exemplary embodiment, the position tracking system 300 may obtain the position information by tracking the location of the uninterested object U according to a magnetic tracking system. Referring to FIG. 20, the position tracking system 300 may include a magnetic field generator IM which is configured for producing magnetic fields, and magnetic sensors MS1, MS2, MS3, and MS4 which are configured for detecting a change in magnetic field.

The magnetic field generator IM may be mounted on the uninterested object U. For this, the magnetic field generator IM may have a form that may be attached to or worn by the uninterested object U. For example, the magnetic field generator IM may be arranged in a patch form, as shown in FIG. 20, and thereby configured to be attached to a hand of the user, or configured to be worn by the user like a glove.

The magnetic sensors MS1, MS2, MS3, and MS4 may detect a change in magnetic field, which may occur due to the movement of the magnetic field generator IM. There may be multiple magnetic sensors MS1, MS2, MS3, and MS4 to more precisely detect the change in magnetic field due to the movement of the magnetic generator IM, as shown in FIG. 20, but the number of the magnetic sensors may be freely chosen.

Although the magnetic sensors MS1, MS2, MS3, and MS4 are arranged on the table 109 on which the subject ob is lying down, as shown in FIG. 20, an arrangement of the magnetic sensors MS1, MS2, MS3, and MS4 is not limited thereto. For example, the magnetic sensors MS1, MS2, MS3, and MS4 may be arranged near the X-ray detector (120 of FIG. 1), or arranged to be movable independently with respect to the X-ray imaging apparatus 100b. Alternatively, the magnetic sensors MS1, MS2, MS3, and MS4 may have a form that may be attached or mounted onto the subject ob.

The position tracking system 300 may obtain the position information by tracking the location of the subject ob based on a change in magnetic field output by the magnetic sensors MS1, MS2, MS3, and MS4. For example, when the user's hand is moving toward the right hand RH of the subject ob, the magnetic field generator IM may move toward the fourth magnetic sensor MS4. Accordingly, the intensity of the magnetic field detected by the first magnetic sensor MS1 may become weak while the intensity of the magnetic field detected by the fourth magnetic sensor MS4 becomes strong, and directions of the magnetic fields detected by the multiple magnetic sensors MS1, MS2, MS3, and MS4 may vary as well. Therefore, based on the change in magnetic field detected by the magnetic sensors MS1, MS2, MS3, and MS4, the position tracking system 300 may track the real-time location of the uninterested object U.

The position information obtained by the position tracking system 300 may be sent to the control processor 180. The control processor 180 may establish the uninterested region UR based on the received position information.

In particular, the control processor 180 may predict the movement of the uninterested object U based on the position information sent from the position tracking system 300. The control processor 180 may determine if the uninterested object U would enter into the scanning region FOV based on the predicted movement of the uninterested object U. If it is predicted that the uninterested object U would enter into the scanning region FOV, the control processor 180 may set up a region into which the uninterested object U is expected to enter as the uninterested region UR in advance.

Furthermore, the control processor 180 may use both the position information obtained by the position tracking system 300 and the X-ray image in order to detect the uninterested object U more accurately.

In an exemplary embodiment, the control processor 180 may use the X-ray image to detect the location, the size, the shape, and the movement of the uninterested object U, as described above, and to compensate the detected location and movement of the uninterested object U based on the position information.

In another exemplary embodiment, the position tracking device 300 may detect the location and movement of the uninterested object U based on the position information, and use the X-ray image to detect the size and shape of the uninterested object U.

In yet another exemplary embodiment, the magnetic field generator IM may be formed to have a special pattern in the X-ray image, which may be used in detecting the uninterested object U in the X-ray image.

FIG. 21 illustrates a position tracking system that uses magnetic fields, according to another exemplary embodiment. While the magnetic field generator IM for producing magnetic fields are attached onto the uninterested object U in FIG. 20, a magnetic sensor MS may be arranged on the uninterested object U.

The magnetic sensor may have a form that may be attached or mounted on the uninterested object U for detecting a change in magnetic field due to the movement of the uninterested object U. For example, the magnetic sensor MS may be arranged in the form of a patch, as shown in FIG. 21, or in the form of a glove that may be worn by the user.

The magnetic field generators IM1, IM2, IM3, and IM4 may be attached or mounted on the object of interest for producing magnetic fields. For example, the magnetic field generators IM1, IM2, IM3, and IM4 may be attached near the scanning area FOV established for the subject ob, as shown in FIG. 21, but is not limited thereto. In another example, the magnetic field generators IM1, IM2, IM3, and IM4 may be mounted on the table 109 on which the subject ob lies, or placed separately from the X-ray imaging apparatus 100b.

Furthermore, although there are four magnetic field generators IM1, IM2, IM3, and IM4 attached to the subject ob in FIG. 21, the number of the magnetic field generators is not limited thereto. The magnetic field generators IM1, IM2, IM3, and IM4 and the table may be integrated in one unit.

The position tracking system 300 may obtain the position information by tracking the location of the subject ob based on a change in magnetic field output by the magnetic sensor MS.

In particular, while the user's hand is moving, the distance between the magnetic field generator IM and the magnetic sensor MS changes, leading to variations in a direction and an intensity of the magnetic field detected by the magnetic sensor MS attached on the user's hand. Therefore, based on the change in magnetic field detected by the magnetic sensor MS, the position tracking system 300 may track the location of the uninterested object U.

While the location of the uninterested object U is tracked based on the variation in magnetic field in FIGS. 20 and 21, how to track the location of the uninterested object U is not limited thereto. For example, the position tracking system 300 may track the location of the uninterested object U according to an optical tracking system.

In the case of tracking the uninterested object U by using an optical tracking system, the position tracking system 300 may include an optically identifiable optical marker and a camera which is configured for capturing the optical marker.

The optical marker refers to an identification mark distinguished from other things in the vicinity, e.g., from the subject ob in the image obtained via the camera, and may be arranged on the uninterested object U.

For example, the optical marker may have a complementary color with respect to a color of the subject ob or the uninterested object U, or the optical marker may have a particular pattern. The optical marker having a particular pattern may be an augmented reality (AR) marker used in AR, but is not limited thereto.

The camera may track the location of the uninterested object on which the optical marker is attached, by detecting the optical marker in the obtained image.

Figure 22:
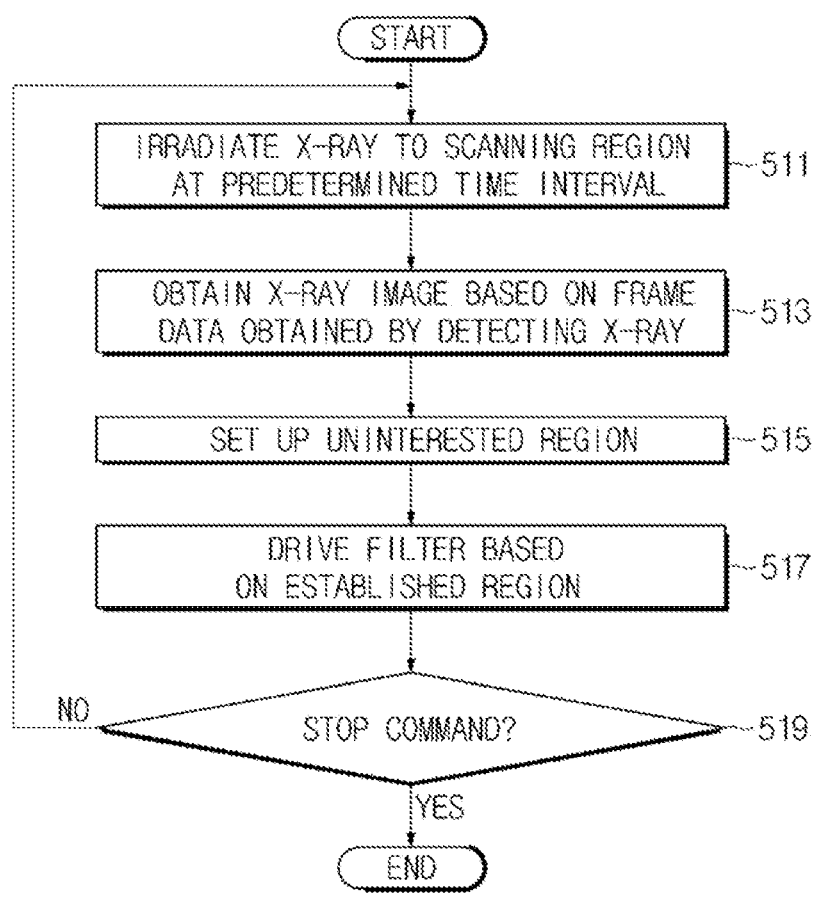
FIG. 22 is a flowchart illustrating a method for controlling an X-ray imaging apparatus, according to an exemplary embodiment.

FIG. 22 is a flowchart illustrating a method for controlling an X-ray imaging apparatus, according to an exemplary embodiment.

Referring to FIG. 22, the X-ray imaging apparatus 100 irradiates X-rays toward a subject region at predetermined regular intervals, in operation 511. In particular, the X-ray source 110 irradiates X-rays toward the subject ob by generating the X-rays according to a predetermined scanning parameter. The scanning parameter may be at least one selected from among a tube voltage, a tube current, an exposure time, a filter type, a frame rate, a pulse rate, a type of target material, and the like. The scanning area FOV into which the X-rays are irradiated may be controlled by the collimator 230. In this aspect, the X-ray imaging apparatus 100 may drive the collimator 230 to irradiate X-rays only into a region requiring its X-ray video.

The X-ray imaging apparatus 100 may obtain the X-ray image based on frame data obtained by detecting the X-rays, in operation 513. The frame data may be obtained in synchronization with the irradiation of X-rays by the X-ray source 110, and an X-ray image may be obtained according to respective pixel values of the frame data.

The X-ray imaging apparatus 100 sets up an uninterested region, in operation 515. The uninterested region UR may be set up to be a specific part of the scanning region FOV. The uninterested region UR may be set up to include the uninterested object U. The uninterested object U refers to an object for which obtaining its X-ray image is not desired, which may include a part of the user who performs a treatment or operation on the subject ob.

Since the uninterested region UR may be set up based on the uninterested object U, the uninterested object U may be detected before the establishment of the uninterested region UR. There are no limitations on how to detect the uninterested object U. In an exemplary embodiment, characteristics of the uninterested object U may be stored in advance from an X-ray image, and based on the stored characteristics, the uninterested object U may be detected by searching an X-ray image obtained in real time.

In another exemplary embodiment, a marker having a special pattern in the X-ray image may be attached onto the uninterested object U, and the uninterested object U may then be detected by searching the X-ray image for the special pattern.

In yet another exemplary embodiment, the uninterested object U may be detected by the position tracking system 300 as shown in FIG. 19. The position tracking system 300 may track the location of the uninterested object U by using either of a magnetic tracking system or an optical tracking system.

Once the uninterested object U is detected, an uninterested region UR may be set up to include the uninterested object U. The location, size, and shape of the uninterested region UR may be determined by taking into account the characteristics, such as the location, size, shape, etc., of the uninterested object U. In particular, the uninterested region UR may be set up around a location that corresponds to the uninterested object U, and the size of the uninterested region UR may be determined to cover the entire uninterested object U.

The uninterested region UR may be set up in an asymmetrical shape, as shown in FIG. 5. If the uninterested region UR is set up to be unnecessarily large in size for the purpose of reducing the exposure of the uninterested object U to irradiation, the X-ray imaging apparatus 100 may be unable to provide sufficient information about the subject ob to the user. Hence, the X-ray imaging apparatus 100 may set up the uninterested region UR to have an asymmetrical shape based on the shape of the uninterested object U. The shape of the uninterested region UR may be determined based on the shape of the detected uninterested object U, or based on the shape of a filtering region formed by the uninterested region filter 210.

The size of the uninterested region UR may be determined based on the movement of the uninterested object U. For example, the control processor 180 may set up the uninterested region UR to be relatively large if the uninterested object U makes a relatively large movement, and relatively small if the uninterested object U makes a relatively small movement.

The control processor 180 may predict the movement of the uninterested object U, and set up the uninterested region UR based on the predicted movement of the uninterested object U. In particular, the control processor 180 may calculate a movement direction and a movement speed of the uninterested object U by tracking the uninterested object U in the X-ray image. Based on the calculated movement speed and the calculated movement direction of the uninterested object U, the control processor 180 may predict the movements of the uninterested object U, and then set up the uninterested region U to include a region into which the uninterested object U is predicted to move.

The X-ray imaging apparatus 100 drives the filter based on the established region, in operation 517. In particular, the X-ray imaging apparatus 100 may control the uninterested region filter 210 to reduce the dosage amount of X-rays to be irradiated to the uninterested region UR. More specifically, the uninterested region filter 210 may form a filtering region that corresponds to the uninterested region UR, by being moved by the filter driver 220 on the x-y plane or along the z-axis, or by changing the shape of the filtering region.

The X-ray imaging apparatus 100 may stop the process if receiving a stop command, or proceed to operation 511 if receiving no stop command, in operation 519. According to the exemplary embodiment, the X-ray imaging apparatus 100 may minimize the X-rays irradiated to the uninterested object U by dynamically setting up the uninterested region while monitoring the uninterested object in an X-ray video.

Figure 23:
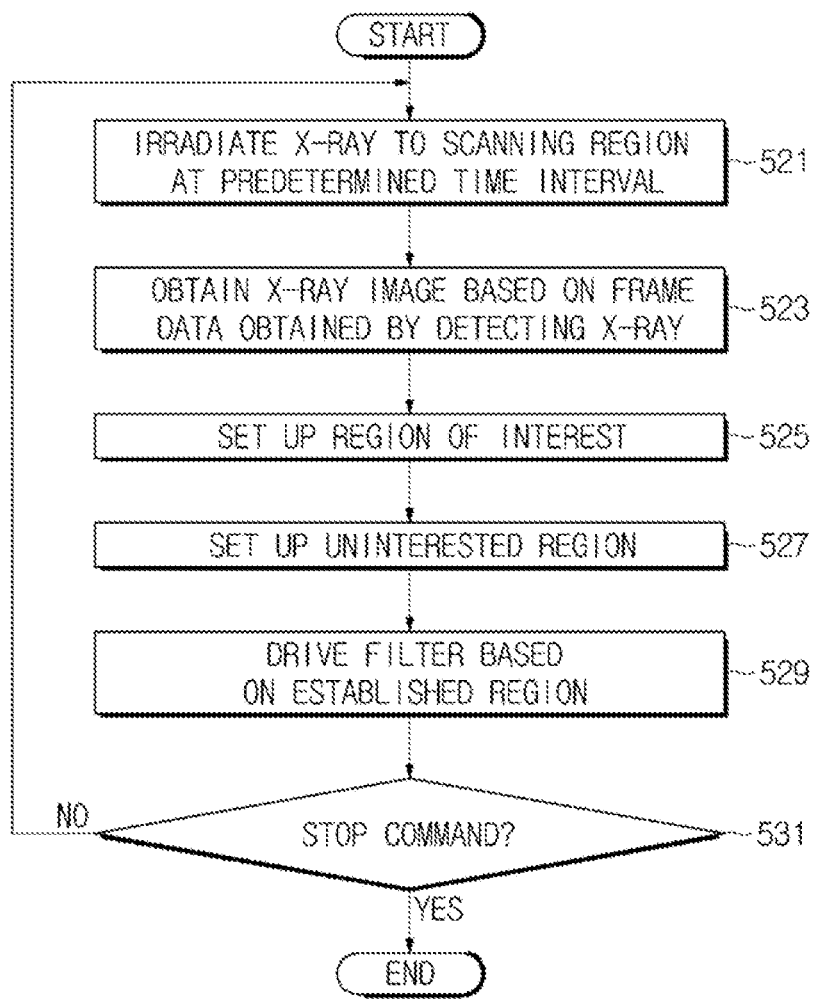
FIG. 23 is a flowchart illustrating a method for controlling an X-ray imaging apparatus, according to another exemplary embodiment.

FIG. 23 is a flowchart illustrating a method for controlling an X-ray imaging apparatus, according to another exemplary embodiment. Referring to FIG. 23, the X-ray imaging apparatus 100 irradiates X-rays toward a subject region at predetermined regular intervals, in operation 521. In particular, the X-ray source 110 irradiates X-rays toward the subject ob by generating the X-rays according to a predetermined scanning parameter.

The X-ray imaging apparatus 100 obtains the X-ray image based on frame data obtained by detecting the X-rays, in operation 523. If there is a background region BR or uninterested region UR of the scanning region FOV, into which a lower dosage amount of X-rays are irradiated, the X-ray imaging apparatus 100 may restore an X-ray image corresponding to the background region BR or uninterested region UR.

The X-ray imaging apparatus 100 may also execute an image equalization algorithm to match the brightness and contrast of the restored image of the uninterested region UR or background region BR with the brightness and contrast of the image of the region of interest ROI.

The X-ray imaging apparatus 100 sets up a region of interest ROI, in operation 525. The region of interest ROI may be set up to be a certain part of the scanning region FOV. The region of interest ROI is a region that includes an object of interest that needs constant observation in the X-ray video, and a remaining region which lies outside of the region of interest ROI may be referred to as the background region BR.

The object of interest is an object that requires constant attention of the user in the X-ray video, such as a treatment instrument used for the subject ob or a region for treatment. The object of interest may be set up by the user or determined according to a pre-stored protocol. For example, if some information is received, for example, via user input, regarding one or more of the type of a treatment instrument, a type of treatment, a region for treatment, whether to inject contrast media, etc., the X-ray imaging apparatus 100 may select the object of interest based on the received information.

The region of interest ROI may be set up to contain an object of interest. The region of interest ROI may be set up based on the location, movement, and size of the object of interest. In particular, the size of the region of interest ROI may be determined to be proportional to the size of the object of interest, and the size of the region of interest ROI may be determined to be relatively large if the object of interest makes a relatively large movement, or if uncertainty about the movement of the object of interest is great.

Furthermore, the region of interest ROI may be established by reflecting the predicted movement of the object of interest. In particular, the control processor 180 may calculate a movement direction and speed of the object of interest by tracking the movement of the object of interest. The control processor 180 may predict the movement of the object of interest by using the calculated movement direction and the calculated speed, and set up a region of interest ROI to include a region into which the object of interest is predicted to move.

The region of interest may be set up according to an input received from the user. As such, dividing the scanning area FOV into the region of interest ROI and the background region BR may help to minimize the dosage amount of X-rays irradiated to the subject ob and thus reduce the risk of the subject ob being exposed to radiation.

The X-ray imaging apparatus 100 sets up an uninterested region UR, in operation 527. The uninterested region UR may be set up to include the uninterested object U. The uninterested region UR may be set up within the background region BR so as not to overlap the region of interest ROI.

The X-ray imaging apparatus 100 drives the filter based on the established region, in operation 529. In particular, the X-ray imaging apparatus 100 may control the filter for region of interest in order to reduce the dosage amount of X-rays irradiated to the background region BR other than the region of interest ROI. More specifically, the filter for region of interest 250 may form a filtering region that corresponds to the background region BR, by being moved by the filter driver 220 on the x-y plane or along the z-axis, or by changing the shape of the filtering region.

Furthermore, the X-ray imaging apparatus 100 may control the uninterested region filter 210 to reduce the dosage amount of X-rays to be irradiated to the uninterested region UR. More specifically, the uninterested region filter 210 may form a filtering region that corresponds to the uninterested region UR, by being moved by the filter driver 220 on the x-y plane or along the z-axis, or by changing the shape of the filtering region.

The X-ray imaging apparatus 100 may stop the process if a stop command is received, or proceed to operation 521 if no stop command is received, in operation 531. According to the exemplary embodiment, the X-ray imaging apparatus 100 may minimize the X-rays irradiated to the subject and the uninterested object U by dynamically setting up the region of interest and the uninterested region while monitoring the uninterested object and the object of interest in an X-ray video.

Figure 24:
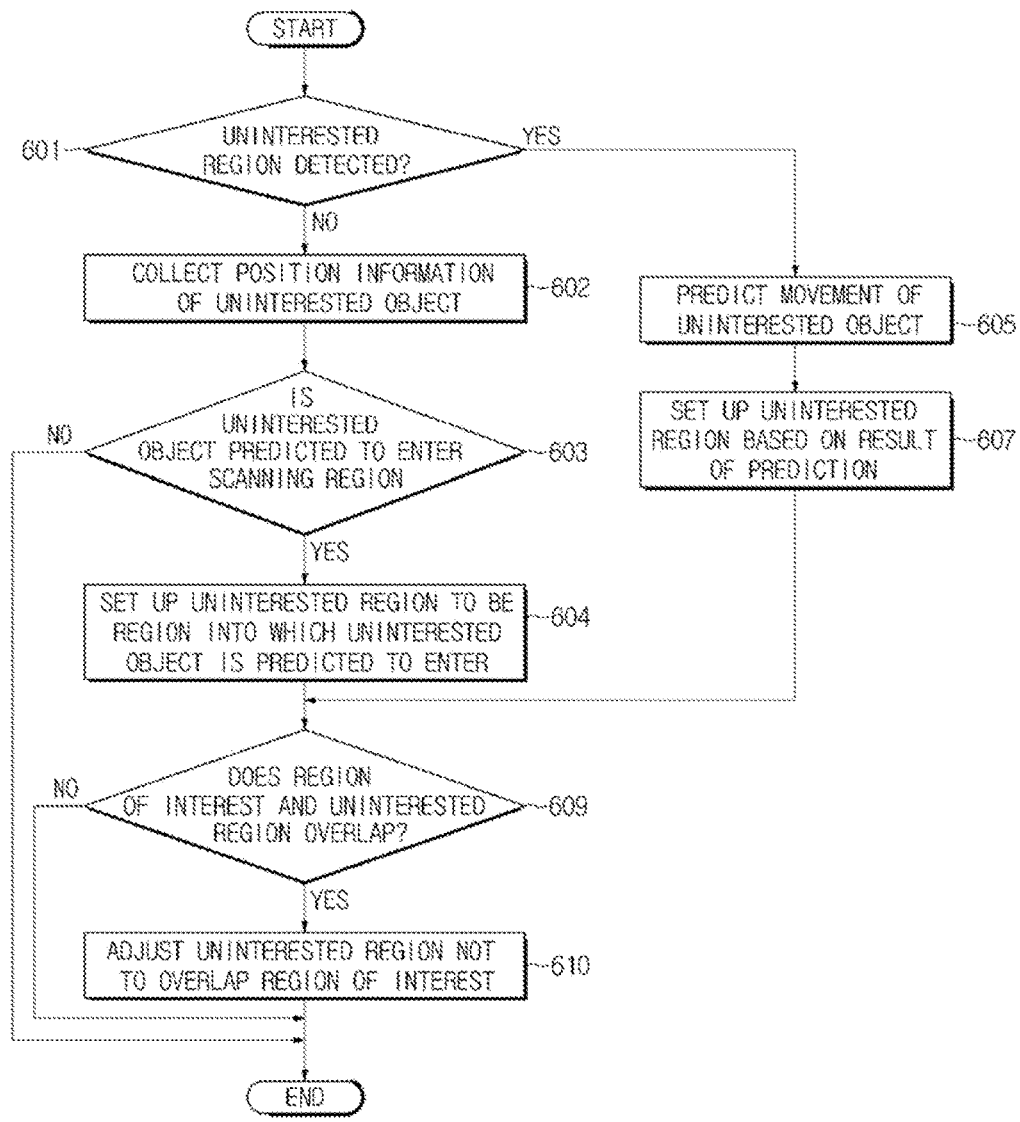
FIG. 24 is a flowchart illustrating a method for establishing an uninterested region, according to an exemplary embodiment.

FIG. 24 is a flowchart illustrating a method for establishing an uninterested region, according to an exemplary embodiment. Given the position tracking system 300 as shown in FIG. 19, the position tracking system 300 may set up the uninterested region UR, by using position information of the uninterested object U obtained by tracking the uninterested object U.

Referring also to FIGS. 19 and 24, the X-ray imaging apparatus 100 determines whether the uninterested object U is detected, in operation 601. The X-ray imaging apparatus 100 may detect the uninterested object U in the X-ray image obtained in real time. For detection of the uninterested object U, one or more characteristics of the uninterested object in the X-ray image may be pre-stored, or a marker having a special pattern in the X-ray image may be attached onto the subject ob. In particular, the X-ray imaging apparatus 100 may search for a region having the pre-stored characteristics or the special pattern in the X-ray image, and detect an item that has the pre-stored characteristics or the special pattern as the uninterested object U.

If the uninterested object U is not detected in operation 601, the X-ray imaging apparatus 100 collects position information of the uninterested object U. The position information may be obtained by the position tracking system 300 for tracking the location of the uninterested object U. The position tracking system 300 may obtain the position information by tracking the location of the uninterested object U by using one of the magnetic tracking system and the optical tracking system.

The X-ray imaging apparatus 100 predicts whether the uninterested object U is expected to enter into the scanning region FOV, based on the position information, in operation 603. In particular, by using the movement information of the uninterested object U, such as the movement direction or movement speed of the uninterested object U, a next movement of the uninterested object U may be predicted.

If it is predicted that the uninterested object U will enter into the scanning region FOV in operation 603, the X-ray imaging apparatus 100 sets up the uninterested region UR to be a region into which the uninterested object U is predicted to enter, in operation 604. If the uninterested region UR is set up after the uninterested object U enters into the scanning region FOV, the uninterested object U could momentarily be exposed to a high dosage amount of X-rays. Accordingly, by setting up the uninterested region UR before the uninterested object U enters into the scanning region FOV, the X-ray imaging apparatus 100 may minimize the exposure of the uninterested object U to radiation.

If the uninterested object U is detected in operation 601, the X-ray imaging apparatus 100 predicts the movement of the uninterested object U, in operation 605. To predict the movement of the uninterested object U, the X-ray imaging apparatus 100 may calculate the movement direction and the movement speed of the uninterested object U by tracking the detected uninterested object U. For prediction of the movement of the uninterested object U, the position information of the uninterested object U obtained by the position tracking system 300 may be used. In particular, based on consecutively collected position information of the uninterested object U, the movement direction and movement speed of the uninterested object U may be calculated, based on which the next movement of the uninterested object U may be predicted.

The X-ray imaging apparatus 100 sets up the uninterested region UR based on the result of the prediction, in operation 607. The location, size, and shape of the uninterested region UR may be determined by taking into account the location, size, shape, movement, etc., of the uninterested object U, and the uninterested region UR may be set up to include a region into which the uninterested object U is predicted to move.

The X-ray imaging apparatus 100 may determine whether the region of interest ROI and the uninterested region UR overlap each other, in operation 609. Since an accurate X-ray video for the region of interest ROI may not be obtained if the region of interest ROI and the uninterested region UR are set up to overlap each other, the X-ray imaging apparatus 100 determines whether they overlap each other.

If it is determined that the region of interest ROI and the uninterested region UR overlap each other in operation 609, the X-ray imaging apparatus 100 may adjust the uninterested region UR so as not to overlap the region of interest ROI, in operation 610.

The X-ray imaging apparatus 100 may set up the uninterested region UR just within a region other than the region of interest ROI, as shown in FIG. 24. In this regard, if the uninterested region UR is set up just within the background region BR, operations 609 and 610 may be omitted.

According to the exemplary embodiments, a risk of being exposed to radiation may be reduced for each of a user and a subject of the X-ray imaging apparatus.

Several exemplary embodiments have been described, but a person of ordinary skill in the art will understand and appreciate that various modifications can be made without departing from the scope of the present disclosure.

What is claimed is:

1. An X-ray imaging apparatus comprising:
   an X-ray source configured to irradiate X-rays toward a subject;
   a filter configured to control a dosage amount of X-rays being irradiated toward the subject; and
   a processor configured to detect, by identifying a marker formed on an uninterested object, the uninterested object in an X-ray image obtained based on the irradiated X-rays, to set up an uninterested region within the X-ray image based on the detected uninterested object, and to control the filter to set the dosage amount of X-rays to be irradiated into the uninterested region,
   wherein the processor is further configured to detect the uninterested object in the X-ray image based on pre-stored characteristics of the uninterested object, and to predict a movement of the uninterested object, and to set up the uninterested region based on the predicted movement of the uninterested object, and
   wherein the marker includes at least one from among a substance which has a higher X-rays penetration characteristic than a surrounding area and a radio-opaque substance.

2. The X-ray imaging apparatus of claim 1, wherein the pre-stored characteristics of the uninterested object include at least one from among a shape, a size, a pattern, a movement property, and an X-ray absorption property of the uninterested object.

3. The X-ray imaging apparatus of claim 1, wherein the marker has a predetermined pattern with respect to the X-ray image.

4. The X-ray imaging apparatus of claim 1, further comprising:
   a position tracking system which is configured for tracking a location of the uninterested object.

5. The X-ray imaging apparatus of claim 4, wherein the position tracking system is further configured to track a location of the uninterested object by using at least one from among a magnetic tracking system and an optical tracking system.

6. The X-ray imaging apparatus of claim 5, wherein the position tracking system includes:
   a magnetic field generator which is mounted on the uninterested object and which is configured for producing a magnetic field; and
   a magnetic sensor which is configured for detecting a change in magnetic field caused by a movement of the uninterested object.

7. The X-ray imaging apparatus of claim 4, wherein the position tracking system includes:
   an identification marker which is arranged on or around the subject and which is configured for producing a magnetic field; and
   a magnetic sensor which is arranged on the uninterested object and which is configured for detecting a change in magnetic field caused by a movement of the uninterested object.

8. The X-ray imaging apparatus of claim 4, wherein when the uninterested object is not detected in the X-ray image, the processor is further configured to set up the uninterested region based on a location tracked by the position tracking system.

9. The X-ray imaging apparatus of claim 8, wherein the processor is further configured, when the uninterested object is predicted to move into a scanning region of the X-ray image, to set up the uninterested region to be a region into which the uninterested object is predicted to move.

10. The X-ray imaging apparatus of claim 1, wherein the processor is further configured to set up the uninterested region so as to include the uninterested object according to at least one selected from among a location, a size, a shape, and a movement of the uninterested object.

11. The X-ray imaging apparatus of claim 1, wherein the processor is further configured to set up the uninterested region so as to include a region into which the uninterested object is predicted to move.

12. The X-ray imaging apparatus of claim 1, wherein the filter includes:
   an uninterested region filter formed of a filtration substance that reduces an incidence of X-rays irradiated from the X-ray source; and
   a filter driver configured to drive the uninterested region filter.

13. The X-ray imaging apparatus of claim 12, wherein the uninterested region filter is further configured to form a filtering region that corresponds to the uninterested region, and to reduce a dosage amount of X-rays to be irradiated into the uninterested region.

14. The X-ray imaging apparatus of claim 12, wherein the processor is further configured to set up the uninterested region so as to have an asymmetrical shape, and
   wherein the uninterested region filter is further configured to form the filtering region based on the asymmetrical shape.

15. The X-ray imaging apparatus of claim 14, wherein the uninterested region filter includes:
   a plurality of masks, each of the plurality of masks being formed of the filtration substance that reduces the incidence of X-rays irradiated from the X-ray source; and
   wherein the filter driver is further configured to move the plurality of masks so as to form the filtering region based on the asymmetrical shape.

16. The X-ray imaging apparatus of claim 1, wherein the processor is further configured to detect an object of interest in the X-ray image, and to divide a scanning region of the X-ray image into a region of interest and a background region based on the detected object of interest.

17. The X-ray imaging apparatus of claim 16, wherein the processor further is configured to set up the uninterested region so as not to overlap with the region of interest.

18. The X-ray imaging apparatus of claim 17, wherein the processor is further configured to set up the uninterested region within a part of the background region.

19. The X-ray imaging apparatus of claim 1, wherein the filter includes:
   a region-of-interest filter configured to filter X-rays irradiated into a background region and the uninterested region;
   an uninterested region filter configured to filter X-rays irradiated into the uninterested region; and
   a filter driver configured to drive both of the region-of-interest filter and the uninterested region filter.

20. A method for controlling an X-ray imaging apparatus, the method comprising:
   obtaining an X-ray image by irradiating X-rays toward a subject;
   detecting an uninterested object which is situated outside of the subject in the X-ray image based on pre-stored characteristics of the uninterested object by identifying a marker formed on the uninterested object in the X-ray image;
   setting up an uninterested region in the X-ray image based on information about the detected uninterested object; and
   controlling a dosage amount of X-rays to be irradiated into the uninterested region by driving at least one filter,
   wherein the setting up the uninterested region in the X-ray comprises:
      attempting to detect an uninterested object which is situated outside of the subject in the X-ray image:
      when the uninterested object is not detected, collecting position information based on a change in a magnetic field that is caused by a movement of the uninterested object;
      predicting a movement of the uninterested object based on the collected position information; and
      when the uninterested object is predicted to move into a scanning region of the X-ray image, setting up the uninterested region to be a region into which the uninterested object is predicted to move.

21. The method of claim 20, wherein the setting up the uninterested region in the X-ray image further comprises:
   dividing a scanning region of the X-ray image into a region of interest and a background region; and
   setting up the uninterested region within a part of the background region.

22. The method of claim 21, wherein the controlling the dosage amount comprises:
   driving a region-of-interest filter so as to form a first filtering region that corresponds to the background region; and
   driving an uninterested region filter so as to form a second filtering region that corresponds to the uninterested region.

* * * * *